United States Patent
Inada et al.

(10) Patent No.: US 10,444,229 B2
(45) Date of Patent: Oct. 15, 2019

(54) METHOD OF MEASURING INSULIN RESISTANCE WITH FATTY ACID COMBUSTION, AND COMPOSITION USED HEREIN

(71) Applicant: OTSUKA PHARMACEUTICAL CO., LTD., Chiyoda-ku, Tokyo (JP)

(72) Inventors: Makoto Inada, Osaka (JP); Jun-ichi Kunizaki, Osaka (JP); Kazuki Tobita, Osaka (JP); Hiroshi Motonari, Osaka (JP); Tetsuya Sato, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/776,543

(22) PCT Filed: Mar. 13, 2014

(86) PCT No.: PCT/JP2014/056699
§ 371 (c)(1),
(2) Date: Sep. 14, 2015

(87) PCT Pub. No.: WO2014/142248
PCT Pub. Date: Sep. 18, 2014

(65) Prior Publication Data
US 2016/0146791 A1     May 26, 2016

(30) Foreign Application Priority Data
Mar. 15, 2013    (JP) .................................. 2013-053979

(51) Int. Cl.
*G01N 33/49*     (2006.01)
*G01N 33/50*     (2006.01)
(Continued)

(52) U.S. Cl.
CPC ....... *G01N 33/5088* (2013.01); *A61B 5/0836* (2013.01); *G01N 33/497* (2013.01); *G01N 2458/15* (2013.01); *G01N 2560/00* (2013.01)

(58) Field of Classification Search
CPC ............................. G01N 33/49; G01N 33/50
(Continued)

(56) References Cited

U.S. PATENT DOCUMENTS 4,328,229 A    5/1982   Fujii et al.
4,451,260 A    5/1984   Mitra
(Continued)

FOREIGN PATENT DOCUMENTS

EP    0 411 629 A2    2/1991
EP    0 860 170 A1    8/1998
(Continued)

OTHER PUBLICATIONS

Sidossis, L. S. et al, American Journal of Physiology 1996, 270, E733-E738.*
(Continued)

*Primary Examiner* — Arlen Soderquist
(74) *Attorney, Agent, or Firm* — Finnegan, Henderson, Farabow, Garrett & Dunner, LLP

(57) ABSTRACT

This invention provides a method for measuring insulin resistance of a test subject, and a composition suitably used for the method.
A method for measuring insulin resistance of a test act comprising steps (a) and (b) below, the method using a composition for measuring insulin resistance comprising, as an active ingredient, a $C_{12-38}$ fatty acid labeled with at least one isotope of C, wherein the $C_{12-38}$ fatty acid is converted in the body into labeled carbon dioxide that is excreted in expired air,
(a) intravenously administering the composition to a test subject and collecting expired air; and
(Continued)

(b) determining the ratio of labeled $CO_2$ amount to unlabeled $CO_2$ amount contained in the expired air or the ratio of labeled $CO_2$ amount to total $CO_2$ amount contained in the expired air.

8 Claims, 10 Drawing Sheets

(51) Int. Cl.
  *G01N 33/497* (2006.01)
  *A61B 5/083* (2006.01)

(58) Field of Classification Search
  USPC .............................. 436/129, 133, 181; 544/1
  See application file for complete search history.

(56) References Cited

U.S. PATENT DOCUMENTS

| | | | |
|---|---|---|---|
| 4,790,327 A | 12/1988 | Despotis | |
| 4,830,010 A | 5/1989 | Marshall | |
| 5,233,997 A | 8/1993 | Klein et al. | |
| 5,670,331 A | 9/1997 | Kouni et al. | |
| 5,707,602 A | 1/1998 | Klein | |
| 5,916,538 A | 6/1999 | Kohno et al. | |
| 5,944,670 A | 8/1999 | Katzman | |
| 6,113,875 A | 9/2000 | Nystrom et al. | |
| 6,186,958 B1 | 2/2001 | Katzman et al. | |
| 6,232,448 B1 | 5/2001 | Yoshikubo et al. | |
| 6,294,151 B1 | 9/2001 | Hayakawa et al. | |
| 6,355,416 B1 | 3/2002 | Abramson | |
| 6,432,382 B1 | 8/2002 | Mehta | |
| 6,509,002 B1 | 1/2003 | Kohno et al. | |
| 6,616,941 B1 | 9/2003 | Seo et al. | |
| 6,740,305 B1 | 5/2004 | Ajami | |
| 6,797,256 B2 | 9/2004 | Inada et al. | |
| 7,018,613 B2 | 3/2006 | Nakagawa et al. | |
| 8,883,121 B2 | 11/2014 | Inoue et al. | |
| 2001/0010825 A1 | 8/2001 | Shimizu et al. | |
| 2001/0021499 A1* | 9/2001 | Wielburski | C12N 5/0018 435/4 |
| 2002/0132283 A1 | 9/2002 | Inada et al. | |
| 2002/0187985 A1* | 12/2002 | Cincotta | A61K 31/55 514/250 |
| 2003/0068272 A1 | 4/2003 | Inada et al. | |
| 2003/0129131 A1 | 7/2003 | Inada et al. | |
| 2003/0190283 A1 | 10/2003 | Nakagawa et al. | |
| 2003/0215500 A1 | 11/2003 | Ohta et al. | |
| 2004/0213763 A1 | 10/2004 | Friedman et al. | |
| 2004/0234452 A1 | 11/2004 | Inada et al. | |
| 2005/0147560 A1 | 7/2005 | Yatscoff et al. | |
| 2006/0020440 A1* | 1/2006 | Hellerstein | G01N 33/5088 703/11 |
| 2006/0263296 A1 | 11/2006 | Kinniburgh et al. | |
| 2006/0280681 A1 | 12/2006 | Harano | |
| 2006/0280682 A1 | 12/2006 | Hellerstein | |
| 2007/0248540 A1* | 10/2007 | Hellerstein | A61K 49/0004 424/1.61 |
| 2008/0233048 A1 | 9/2008 | Inoue et al. | |
| 2009/0131810 A1 | 5/2009 | Oren et al. | |
| 2010/0041082 A1 | 2/2010 | Hellerstein | |
| 2010/0055799 A1 | 3/2010 | Inada et al. | |
| 2010/0209385 A1* | 8/2010 | Febbraio | C07K 14/475 424/85.2 |
| 2011/0166792 A1* | 7/2011 | Takahata | G06F 19/3437 702/19 |
| 2012/0003335 A1* | 1/2012 | Xie | A61K 31/444 424/740 |
| 2012/0100073 A1* | 4/2012 | Mach | A61K 51/0402 424/1.89 |
| 2013/0143253 A1 | 6/2013 | Inada et al. | |
| 2014/0087407 A1* | 3/2014 | Deutz | G01N 33/58 435/19 |
| 2014/0135359 A1* | 5/2014 | Martineau | A01N 35/06 514/292 |
| 2014/0329274 A1* | 11/2014 | Bowen | G01N 33/6848 435/34 |
| 2015/0017100 A1 | 1/2015 | Inoue et al. | |
| 2015/0031068 A1* | 1/2015 | Glick | G01N 33/564 435/29 |
| 2015/0204852 A1 | 7/2015 | Inada et al. | |

FOREIGN PATENT DOCUMENTS

| | | |
|---|---|---|
| EP | 1285668 A1 | 2/2003 |
| EP | 1 374 911 A1 | 1/2004 |
| JP | 64-61647 | 3/1989 |
| JP | 2-172918 A | 7/1990 |
| JP | 3-66613 A | 3/1991 |
| JP | 7-300430 | 11/1995 |
| JP | 10-500995 A | 1/1998 |
| JP | 10-67689 | 3/1998 |
| JP | 11-124343 | 5/1999 |
| JP | 2000-507802 | 6/2000 |
| JP | 2002-513911 | 5/2002 |
| JP | 2008-543787 | 12/2006 |
| JP | 4007653 | 11/2007 |
| JP | 2008-44889 A | 2/2008 |
| JP | 2008-531068 A | 8/2008 |
| JP | 2008-536275 A | 10/2008 |
| JP | 2008-292506 | 12/2008 |
| JP | 2009-515139 A | 4/2009 |
| JP | 2010-502194 A | 1/2010 |
| JP | 2010-44093 | 2/2010 |
| JP | 2011-106846 A | 6/2011 |
| JP | 2011-141273 | 7/2011 |
| KR | 20010017804 A | 3/2001 |
| WO | WO 91/18105 A1 | 11/1991 |
| WO | WO 96/14091 | 5/1996 |
| WO | WO 96/36330 A2 | 11/1996 |
| WO | WO 97/02050 | 1/1997 |
| WO | WO 97/35622 A1 | 10/1997 |
| WO | WO 97/40856 A1 | 11/1997 |
| WO | WO 98/09658 A1 | 3/1998 |
| WO | WO 99/56790 | 11/1999 |
| WO | WO 00/61197 A1 | 10/2000 |
| WO | WO 02/072153 A1 | 9/2002 |
| WO | WO 2004/87146 A1 | 10/2004 |
| WO | WO 2006/112513 A1 | 10/2005 |
| WO | WO 2006/090880 A1 | 8/2006 |
| WO | WO 2006/135879 | 12/2006 |
| WO | WO 2007/007100 A2 | 1/2007 |
| WO | WO 07/013409 A1 | 2/2007 |
| WO | WO 2008/028116 A2 | 3/2008 |
| WO | WO 2008/138993 A1 | 11/2008 |
| WO | WO 01/82979 A1 | 8/2011 |

OTHER PUBLICATIONS

Jones, A. E. et al, British Journal of Nutrition 1999, 81, 37-43.*
Blaak, E. E. et al, Journal of Clinical Endocrinology & Metabolism 2001, 86, 1638-1644.*
Kasiske, B. L. Hypertension 1992, 19, Supplement 1, I-110-I-115.*
Boden G., Diabetes 1997, 46, 3-10.*
Pick, A. et al, Diabetes 1998, 47, 358-364.*
Griffin, M. E. et al, Diabetes 1998, 48, 1270-1274.*
Kelley, D. E. et al, American Journal of Physiology. Endocrinology and Metabolism 1999, 277, E1130-E1141.*
Young, M. A. et al, Diabetes 200, 51, 2587-2595.*
Mazumder, P. K. et al, Diabetes 2004, 53, 2366-2374.*
Nolan, C. J. et al, Diabetologia 2006, 49, 2120-2130.*
Turner, N. et a, Diabetes 2007, 56, 2085-2092.*
Koves, T. R. et al, Cell Metabolism 2008, 7, 45-56.*
Storlien, L. H. et al, Diabetes 1991, 40, 280-289.*
Paul, P. et al, American Journal of Physiology 1966, 211, 1313-1320.*
Steele, R, et al, American Journal of Physiology 1968, 214, 313-319.*
Balasse, E. O. et al, European Journal of Clinical Investigation 1974, 4, 247-252.*

(56) References Cited

OTHER PUBLICATIONS

Malmendier, C. L. et al, Journal of Clinical Investigation 1974, 54, 461-476.*
Hall, S. E. H. et al, Diabetologia 1979, 16, 297-306.*
Shaw, J. H. F. et al, American Journal of Physiology 1984, 247, E756-E764.*
Wolfe, R. R. et al, American Journal of Physiology 1985, 248, E236-E243.*
Petrides, A. S. et al, Journal of Clinical Investigation 1991, 88, 561-570.*
Bonadonna, R. C. et al, American Journal of Physiology 1994, 266, E501-E509.*
Laville, M. et al, Metabolism 1995, 44, 639-644.*
van Hall, G., Proceedings of the Nutrition Society 1999, 58, 979-986.*
McCue, M. D. et al, Journal of Experimental Biology 2010, 213, 782-789.*
Shaw, J. H. F. et al, Metabolism 1985, 34, 442-449.*
Delany, J. P. et al, American Journal of Clinical Nutrition 2000, 72, 905-911.*
Kelley, D. E. et al, Diabetes 2000, 49, 677-683.*
Bruce, C. R. et al, American Journal of Physiology—Endocrinology and Metabolism 2006, 291, E99-E107.*
Magkos, F. et al, Clinical Lipidology 2009, 4, 215-230.*
Wensaas, A. J. et al, Diabetes 2009, 58, 527-535.*
Bruce, C. R. et al, Diabetes 2009, 58, 550-558.*
Schenk, S. et al, Journal of Physiology 2009, 587, 4949-4961.*
Zhang, L. et al, Biochimica et Biophysica Acta 2010, 1801, 1-22.*
Bell, J. A. et al, Journal of Clinical Endocrinology and Metabolism 2010, 95, 3400-3410.*
Hodson, L. et al, American Journal of Physiology—Endocrinology and Metabolism 2010, 299, E584-E592.*
Cheng, Z. et al, Trends in Endocrinology and Metabolism 2010, 21, 589-598.*
Orellana-Gavalda, J. M. et al, Heptology 2011, 53, 821-832.*
Gaster, M., Biochemical and Biophysical Research Communications 2011, 404, 1023-1028.*
Carpentier, A. C. et al, Clinical Lipidology 2011, 6, 703-716.*
Vogel-van den Bosch, J. et al, Journal of Nutritional Biochemistry 2011, 22, 366-371.*
Sannocha-Bonet, D. et al, PLoS One 2012, 7, e36320, 8 pages.*
Dillon, E. Licher, "Novel Noninvasive Breath Test Method for Screening Individuals at Risk for Diabetes," Diabetes Care, 32:430-435 (2009).
Extended European Search Report for corresponding EP Application No. 13831608.8 dated Mar. 30, 2016.
Tsuchiya, Masako et al., Evaluation of a novel non-invasive ⁻C-glucose breath test for the Identification of diabetes mellitus in cirrhotic patients, Hepatology Research, vol. 42, No. 12, pp. 1196-1201 (2012).
B. Ravikumar et al., "Real-time assessment of postprandial fat storage in liver and skeletal muscle in health and type 2 diabetes", American Journal of Physiology, Endocrinology and Metabolism, vol. 288, No. 4, pp. E789-E797 (2005).
"Elyo: Hyoka to Chiryo" Japanese Journal of Nutritional Assessment, vol. 29, No. 1, p. 37-40 (2012).
Kagaku no Ryoiki, Journal of Japanese Chemistry, vol. 107, pp. 149-163 (1975).
Nankodo: Kajiwara, Radioisotopes, vol. 41, No. 1. pp. 46-48 (1992).
International Search Report from the Japanese Patent Office for International Application No. PCT/JP2014/056699 dated Jun. 3, 2014.
Mariani et al.; "Radionuclide Gastroesophageal Motor Studies", The Journal of Nuclear Medicine, vol. 45, No. 6, pp. 1004-1028, (2004).
Talley NJet al. "Functional Gastroduodenal Disorders", Gut 45 (Suppl 2): II 37-42, 1999.
Nakada et al., "J. Smooth Muscle Res. (Jpn. Sec.) 6:J-75-J-91, 2002."
Kitagawa et al. "J. Smooth Muscle Res. (Jpn. Sec.) 6:J-129-J-138, 2002."
Sasaki, "5.1 Use of Stable Isotopes in Clinical Diagnosis," Kagaku no Ryoiki 107 "Use of Stable Isotopes in Medicine, Pharmacy and Biological," pp. 149-163 (1975) Nankodo.
Mion, Francois; et al; "13CO2 breath test : comparison of isotope ratio mass spectrometry and non-dispersive infrared spectrometry results" Gastroenterologie Clinique et Biologique, 25, 375-379, 2001.
International Search Report for International Application No. PCT/JP2007/058039, dated Jul. 10, 2007, and cited in related U.S. Appl. No. 12/295,631, filed Oct. 9, 2001.
Braden, Barbara et al., "The [$^{13}$C]Acetate Breath Test Accurately Reflects Gastric Emptying of Liquids in Both Liquid and Semisolid Test Meals." Gastroenterology, vol. 108, No. 4, pp. 1048-1055, 1995.
Breen, Peter H. et al., "Measurement of blood $Co_2$ conventional $Pco_2$ analyzer," Critical Care Medicine, vol. 24, No. 7, pp. 1215-1218, 1996.
Creasey, William A., et al., "The metabolism of uracil-2-$^{14}$C and the granulocyte response to endotoxin as indicators of the toxity produced in patients receiving 5-fluorouracil," Clinical Pharmacology and Therapeutics, vol. 8, No. 2, pp. 273-282, 1967
Fernandez-Salguero, Pedro, et al., "Correction Between Catalysis Activity and Protein Content for the Polymorphically Expressed Dihydropyrimidins Dehydrogenase in Human Lymphocytes," Biochemical Pharmacology, vol. 50, No. 7, pp. 1015-1020, 1995.
Fleming, Ronald A., et al., "Correlation between Dihydropyrimidine Dehydrogenase Activity in Peripheral Mononuclear Cells and Systemic Clearance of Fluorouracil in Cancer Patients," Cancer Research, vol. 52, pp. 2899-2902, 1992.
Gan, K.H. et al., "Effect of Omerprazole 40mg Once Daily on Intraduodenal and Intragastric pH in H. Pylori-Negative Healthy Subjects," Digestive Diseases and Sciences, vol. 42, No. 11, pp. 2304-2309, 1997.
Geus, W.P., et al., "Pharmacodynamics and kinetics of omeprazole MUPS 20 mg and pantoprazole 40 mg during repeated oral administration in Helicobacter pylori-negative subjects," Alimentary Pharmacology & Therapeutics, vol. 14, pp. 1057-1064, 2000.
Johnson, Martin R., et al., "Semi-automated radioassay for determination of dihydropyrimidine dehydrogenase (DPD) activity Screening cancer patients for DPD deficiency, a condition associated with 5-fluorouracil toxicity," Journal of Chromatography B, vol. 696, pp. 183-191, 1197.
Lehman, K., "Acrylic Latices from Redisperable Powders for Peroral and Transdermal Drug Formulations," Drug Development and Industrial Pharmacy, vol. 12, No. 3, p. 265-287, 1986.
Meineke, I., et al., "Evaluation of the $^{13}CO_2$ kinetics in humans after oral application of sodium bicarbonate as a model for breath testing," European Journal of Clinical Investigation, vol. 23, No. 2, pp. 91-96, 1993.
Ogata, Hiroyasu, et al., "Development and Evaluation of a New Peroral Test Agent GA-test for Assessment of Gastric Acidity," J. Pharm. Dyn., vol. 7, pp. 656-664, 1984.
Sato, T., et al., "Evaluation of Immunological Rapid Urease Testing for Detection of Helicobacter pylori," European Journal of Clinical Microbiology & Infectious Diseases, vol. 19, pp. 438-442, 2000.
Sjövall., H., et al. "Simultaneous Measurement of Gastric Acid and Bicarbonate Secretion in Man." Scandinavian Journal of Gastroenterology, vol. 24, No. 10, pp. 1163-1171, 1989.
Sumi, Satoshi, et al., "Automated screening system for purine and pyrimidine metabolism disorders using high-performance liquid chromatography," Journal of Chromatography B, vol. 672, pp. 233-239, 1995.
Sumi, Satoshi, et al., "Possible prediction of adverse reactions to fluorouracil by the measurement of urinary dihydrothymine and thymine," International Journal Molecular Medicine, vol. 2, pp. 477-482, 1998.
Triplett, J.W., et al., "Synthesis of Carbon-13 Labelled Uracil, 6,7-Dimethyllumazine, and Lumichrome, Via a Common Intermedicine: Cyanoacetylurea," Jornal of Labelled Compounds and Radiopharmaceuticals, vol. 14, No. 1, pp. 35-41, 1978.

(56) References Cited

OTHER PUBLICATIONS

Van Kuilenburg, André B.P., et al., "Pitfalls in the Diagnosis of Patients with a Partial Dihydropyrimidine Dehydrogenase Deficiency," *Clinical Chemistry*, vol. 46, No. 1, pp. 9-17, 2000.
Supplementary Partial European Search Report Issued in EP Application No. 01941167, dated Nov. 1, 2004, 3 pages, as cited in related U.S. Appl. No. 13/817,349, filed Feb. 15, 2013.
Supplementary European Search Report for EP Application No. 01925887, dated May 25, 2007, 4 pages, as cited in related U.S. Appl. No. 13/817,349, filed Feb. 15, 2013.
Clough, Michael R.I. et al., "The Calcium Carbonate Breath Test, a noninvasive test of stimulated gastric acid secretion: preliminary communication," *Eur J Gastroenterol Hepatol.*, vol. 21, No. 3, pp. 266-272, Mar. 2009.
Wetzel, Klaus, et al., "$^{13}$C-Breath Tests in Medical Research and Clinical Diagnosis," *Fischer ANalysen Instrumente GmbH*, 4$^{th}$ Edition, May 2005, 66 pages.
Supplementary European Search Report issued in EP Application No. 11818231, dated Jan. 23, 2014, 6 pages, as cited in related U.S. Appl. No. 13/817,349, filed Feb. 15, 2013.
Hiroaki Kubo et al., Enhancement of Oral Bioavailability and and Pharmaceutical Effect of 1-(3-4-Dimethoxyphenyl)-2,3-bis(methoxycarboryl)-4-hydroxy-6,7,8-trimethoxynaphthalene (TA-7552), a New Hypocholesterolemic Agent, by Micronization in Co-ground Mixture with D-Mannitol, Biological and Pharmaceutical Bulletin, vol. 19, No. 5, 1996, pp. 741-747.
European Search Report dated Jun. 8, 2007 for European Application No. 01925887.0., as cited in the information disclosure Statement dated Jun. 27, 2011 in related U.S. Appl. No. 11/989,285, filed Jan. 24, 2008.
European Search Report dated Mar. 23, 2011 for European Application No. 07741475 3., as cited in the information disclosure Statement dated Jun. 27, 2011 in related U.S. Appl. No. 11/989,286, filed Jan. 24, 2008.
Braden, B. et al., "$^{13}$C-breath tests: Current State of the Art and Future Directions," *Dig. Liver Dis.* 39(9):795-805 (2007).
Choi, M.G. et al., "Reproducibility and Simplification of $^{13}$C-Octanoic Acid Breath Test for Gastric Emptying of Solids," *Am. J. Gastroenterol.* 93:92-8 (1998).
Ghoos, Y.F., et al, "Measurement of Gastric Emptying Rate of Solids by Means of a Carbon-Labeled Octanoic Acid Breath Test," *Gastroenterology* 104:1640-7 (1993).
Glerup, H. et al., "Gastric Emptying: A Comparison of Three Methods," *Scand. J. Gastroenterol.* 42:1182-86 (2007).
Herting, D.C. et al., "Absorption of Acetic Acid and Glycerol From the Rat Stomach," *Am. J. Physiol.* 187:224-26 (1956).
Inada, M. et al., "Pharmacokinetic modelling of [2-$^{13}$C]Uracil Metabolism in Normal and DPD-Deficient Dogs," *Nucleosides, Nucleotides, and Nucleic Acids* 25:1205-9 (2006).
Inada, M. et al., "Relationships Among Plasma [2-$^{13}$C]Uracil Concentrations, Breath $^{13}CO_2$ Expiration, and Dihypropyrimidine Dehydrogenase (DPD) Activity in the Liver in Normal and DPD-Deficient Dogs," *Drug Metabolism and Disposition* 33(6):381-87 (2005).
Irving, C.S. et al., "[$^{13}$C]bicarbonate kinetics in humans: intra—vs. interindividual variations," *Amer. J. Physiol.* 245(2):R190-R202 (1983).
Ito, S. et al., "Physiologically based pharmacokinetic modelling of the three-step metabolism of pyrimidine using $^{13}$C-uracil as an in vivo probe," *Br. J. Clin Pharmacol.* 60:584-93 (2005).
Karamanolis, G. et al., "Association of the Predominant Symptom With Clinical Characterization and Pathophysiological Mechanisms in Functional Dyspepsis," *Gastroenterology* 130:296-303 (2006).
Lu, Z. et al., "Decreased Dihydropyrimidine Dehydrogenase Activity in a Population of Patients with Breast Cancer: Implication for 5-Fluorouracil-based Chemotherapy," *Clin. Cancer Res.* 4:325-29 (1998).
Maes, B.D. et al., "$^{13}$C-Octanoic Acid Breath Test for Gastric Emptying Rate of Solids," *Gastroenterol.* 114:856-59 (1998).

Maes, B.D. et al., "Combined Carbon-13-Glycine/Carbon-14-Octanic Acid Breath Test to Monitor Gastric Emptying Rates of Liquids and Solids," *J. Nuc. Med.* 35(5):824-31 (1994).
Mattison, L K et al., "The Uracil Breath Test in the Assessment of Dihydropyrimidine Dehydrogenase Activity: Pharmacokinetic Relationship between Expired $^{13}CO_2$ and Plasma [2- $^{13}$C]Dihydrouracil," *J. Am. Assoc. Cancer Res.* 12(2):549-55 (2006).
Quartero, A.O. et al., "Distributed Solid-Phase Gastric Emptying in Functional Dyspepsia: A Meta-Analysis," *Dig. Diseases and Sciences.* 43:2028-33 (1998).
Sanaka, M. et al. "Comparison Between Gastric Scintigraphy and the [$^{13}$C]-Acetate Breath Test with Wagner-Nelson analysis in Humans," *Clin Exp. Pharmacol. Physiol.* 33:1239-43 (2006).
Sanaka, M. et al., "The Wagner-Nelson Method Makes the [$^{13}$C]-Breath Test Comparable to Radioscintigraphy in Measuring Gastric Emptying of a Solid/Liquid Mixed Meal in Humans," *Clin Exp. Pharmocol. Physiol.* 34:641-44 (2007).
Schneider, A.R. et al., "Total Body Metabolism of $^{13}$C-octanoic Acid is Patients with Non-Alcoholic Steatohepatitis, But Differs Between Women and Men," *Eur. J. Gastroenterology. Hepatol.* 17:1181-84 (2005).
Stranghellini, V. et al., "Risk Indicators of Delayed Gastric Emptying of Solids in Patients With Functional Dyspepsia," *Gastroenterol.* 110:1036-42 (1996).
Sugiyama, E. et al., "Desirable Pharmacokinetic Properties of $^{13}$C-uracil as a Breath Test Probe of Gastric Emptying in Comparison with $^{13}$C-acetate and $^{13}$C-octanoate in Rats," *Scand J. Gastroenterol.* 44:1067-75 (2009).
Tack, J., "Gastric Motor Disorders," *Best Pract. Res. Clin. Gastroenterology.* 21:633-44 (2007).
Tazawa, S. et al., "KDR-5169, a New Gastrointestinal Prokinetic Agent, Enhances Gastric Contractile and Emptying Activities in Dogs and Rats," *Eur J. Pharmacol.* 434:169-76 (2002).
Votruba, S.B. et al., "Validation of Deuterium Labelled Fatty Acids for the Measurement of Dietary Fat Oxidation: a Method for Measuring Fat-Oxidation in Free-Living subjects," *Int. J. Obes. Relat. Metab. Disord.* 25:1240-45 (2001).
Yen, J.L. et al., "Should DPD Analysis be Required Prior to Prescribing Pluoropyimidines?" *Eur. J. Cancer* 43:1011-16 (2007).
Iida, et al., "Synthesis of $^{13}$ C-Labelled Compounds having a Urea Unit, and Observations of $^{13}$ C-Isotope Effect in Their Infrared Spectra" J. Labelled Cmpd. Radiopharmaceuticals—vol. XXXIX, No. 1, 1997, 39, 69-77.
The Merck Index, Merck Research Laboratories Division of Merck & Co., Inc., 2001, 13th Edition, pp. 1755-1756, No. 9918. Uracil.
International Search Report from Japanese Patent Office for International Application No. PCT/JP2013/072204, dated Sep. 24, 2013, cited in related U.S. Appl. No. 14/423,021, filed Feb. 20, 2015.
Office Action dated Oct. 11, 2012, in related U.S. Appl. No. 11/989,286, filed Jan. 24, 2008.
Office Action dated Apr. 9, 2013, in related U.S. Appl. No. 11/989,286, filed Jan. 24, 2008.
Singal et al. "Intra-Individual Variability of Co $^2$ Breath Isotope Enrichment Compared to Blood Glucose in the Oral Glucose Tolerance Test" Diabetes Technology & Therapeutics, vol. 12, No. 12, 2010, pp. 947-953
Office Action dated Jul. 20, 2016, cited in related U.S. Appl. No. 14/423,021, filed Feb. 20, 2015.
Dillon, E. Lichar, "Novel Noninvasive Breath Test Method for Screening Individuals at Risks for Diabetes," Diabetes Care, 32, 430-435 (2009).
Extended European Search Report for EP Application No. 13831608.8 dated Mar. 30, 2016, which coresponds to related U.S. Appl. Nos. 14/423,021, filed Feb. 20, 2015, and U.S. Appl. No. 14/776,543, filed Sep. 14, 2015( the present patent application).
Tsuchiya, Masako et al., "Evaluation of a novel-invasive $^{13}$C-glucose breath test for the Identification of diabetes melitus in cirrhotic patients."Hepatology Research, vol. 42, No. 12, pp. 1196-1201 (2012).
Supplementary European Search Report dated Oct. 7, 2016 for EP Application No. 14/763,271.
Savarino, V. et al., "The $^{13}$C urea breath test in the diagnosis of Helicobacter pylori infection," Gut 1999; 45 (Suppl I), 118-122.

(56) References Cited

OTHER PUBLICATIONS

Abel, "Free Fatty Acid Oxidation in Insulin Resistance and Obesity," Heart Metab., 2010, 48:5-10.
Herrero et al., "Increased Myocardial Fatty Acid Metabolism in Patients With Type 1 Diabetes Mellitus," J Am Coll Cardiol., 2006, 47(3):598-604.

* cited by examiner (A)

(B)

(A)

(B)

METHOD OF MEASURING INSULIN RESISTANCE WITH FATTY ACID COMBUSTION, AND COMPOSITION USED HEREIN

This application is the U.S. National Stage of PCT application PCT/JP2014/056699 filed Mar. 13, 2014, that claims priority to Application No. JP2013-053979 filed in Japan on Mar. 15, 2013.

TECHNICAL FIELD

The present invention relates to a method for measuring the presence or absence of insulin resistance in a test subject, and a composition suitably used for the method. More specifically, the present invention relates to a method for measuring and monitoring the presence or absence of insulin resistance in a test subject based on the fatty acid combustion of the test subject by performing a breath test using labeled carbon such as $^{13}C$ etc.; and a composition suitably used for the method. The aforementioned "method for measuring the presence or absence of insulin resistance in a test subject" includes a method for determining whether a hyperinsulinemia test subject has insulin resistance or not. The former case enables the test subject to be determined as "insulin-resistant," and the latter case enables the test subject to be determined to have "hyperinsulinemia without insulin resistance" (hereinafter may also be referred to as "insulin-nonresistant hyperinsulinemia").

Further, the present invention relates to a method for measuring a sugar/fatty acid combustion ratio in a test subject using a labeled C-breath test, and a composition suitably used for the method.

BACKGROUND ART

Abnormal glucose tolerance generally designates a state where the fasting blood glucose level is in a range of 110 mg/dl to less than 126 mg/dl, or a state where the 2-hour value in an oral glucose tolerance test is 140 mg/di to 199 mg/dl, and is also called borderline diabetes. Although the patients of borderline diabetes have abnormal blood glucose levels, they are not exactly considered to have diabetes; however, if the patients leave the condition untreated, they are highly likely to become diabetic. The condition is thus called prediabetes. Further, arteriosclerosis is known to advance at this stage. Therefore, in terms of preventive medicine as well, it is important to detect patients in a prediabetic stage.

In the diagnosis of diabetes, primary screening is generally conducted first with a urine glucose test or a fasting blood glucose level test, and, if such tests are positive, a glucose tolerance test is performed to make a definite diagnosis. In recent years, HbA1C or fructosamine in the blood may also be tested before a glucose tolerance test using glucose.

However, side effects caused by administration of a large amount of glucose have been indicated with regard to the glucose tolerance test using glucose. Further, the test requires test subjects to be restrained for several hours, and for blood to be repeatedly collected. Because this therefore imposes a great physical burden on test subjects, the test can only actually be carried out on a limited number of test subjects. Further, the results of HbA1C or fructosamine cannot be known until the next hospital visit, thus posing the drawback of insufficient rapidity. The tests performed before these tests, such as the urine glucose test or fasting blood glucose level test, have problematic low sensitivity since they often show negative results of urine glucose or normal results of blood glucose levels even though the test subjects are diabetic; thereby, they miss many cases of diabetic patients. Accordingly, these known methods for diagnosing diabetes are incapable of determining a prediabetic stage in which diabetes has not yet been developed, such as borderline diabetes, or a condition even before borderline diabetes (a condition having insulin resistance or hyperinsulinemia without insulin resistance).

In recent years, as a diabetes diagnosis method, a method of intravenously administering acetic acid, oleic acid, or palmitic acid labeled with $^{13}C$, and measuring the increasing rate of $^{13}C$ concentration in the $CO_2$ in the expired air with a breath test, thereby diagnosing insulin hyposecretion-type diabetes has been suggested (Patent Document 1). However, it is unknown whether this method is capable of diagnosing a condition even before borderline diabetes (a condition having insulin resistance or hyperinsulinemia without insulin resistance).

Examples of underlying diseases showing insulin resistance include liver diseases. In particular, liver cirrhosis patients have a nutritionally typical pathological condition of protein-energy malnutrition (PEM). Moreover, a significant percentage of the liver cirrhosis patients also have comorbid insulin resistance. Thus, a correlation between comorbid insulin resistance and liver cancer has also been reported. However, a method for diagnosing comorbid insulin resistance in liver cirrhosis patients has not been established. For the diagnosis of PEM degree, indirect calorimetry for detecting saccharideilipid combustion ratio has been used. The saccharide/lipid combustion ratio can be calculated as a respiratory quotient. It has been reported that the prognosis of liver cirrhosis or liver cancer worsens when the respiratory quotient is decreased to 0.85 or less by a decrease in saccharide combustion and/or an increase in fat combustion. Further, it has also been reported that the respiratory quotient significantly decreases with the increase in severity of liver cirrhosis (Non-patent Document 1). More specifically, by measuring the saccharide/lipid combustion ratio, it is possible to determine the prognosis or severity of liver cirrhosis, liver cancer, etc. However, known methods using calculation of respiratory quotient have little practicability, and it is considered impossible to easily grasp the nutritional status objectively.

Meanwhile, applying so-called a labeled C-breath test, which is a method of measuring $^{13}CO_2$ excreted in expired air as carbon dioxide after administration of $^{13}C$-labeled glucose, to the diagnosis of diabetes has been proposed (Patent Documents 2 to 4). More specifically, Patent Document 2 discloses a method for diagnosing the presence or absence of diabetes as well as the type of diabetes (type I diabetes or type II diabetes) by performing a breath test using glucose wherein the carbon at a specific position is replaced by $^{13}C$, and determining the degree of increase in $^{13}CO_2$ concentration excreted in expired air. Further, Patent Documents 3 and 4 disclose performing a breath test using $^{13}C$-labeled glucose as in Patent Document 2 and diagnosing a diabetic patient or an insulin-resistant patient based on an index such that the ratio of $^{13}C$ to $^{12}C$ ($^{13}C/^{12}C$) in expired air that is lower than the ratio of a healthy subject, the ratio being calculated from the concentration of $^{13}CO_2$ excreted in the expired air.

However, these documents nowhere disclose or suggest combining a labeled C-breath test using glucose with a labeled C-breath test using fatty acid, thereby enabling highly accurate detection of a saccharide/lipid combustion ratio that can replace respiratory quotient.

CITATION LIST

Patent Documents

Patent Document 1: JPH11-124343A
Patent Document 2: JPH10-67689A
Patent Document 3: JP2002-513911A
Patent Document 4: JP2008-292506A Non-patent Documents Non-patent Document 1: "Eiyo: Hyoka to Chiryo" Japanese Journal of Nutritional Assessment, vol. 29, No. 1, page 37-40

SUMMARY OF INVENTION

Technical Problem

An object of the present invention is to provide a method for detecting insulin resistance in a test subject rapidly and with high accuracy with a labeled C-breath test using isotope-labeled $C_{12\text{-}38}$ fatty acid. Another object of the present invention is to provide a composition to be used for insulin resistance measurement in the above method.

Still another object of the present invention is to provide a method for detecting a sugar/fatty acid combustion ratio and insulin resistance in a test subject with high accuracy by combining a result of a labeled C-breath test using isotope-labeled $C_{12\text{-}38}$ fatty acid with a result of a labeled C-breath test using isotope-labeled glucose or a blood glucose level.

Solution to Problem

The present inventors conducted extensive research to achieve the above objects, and found that insulin resistance in a test subject can be measured rapidly and with high accuracy based on the behavior of the amount of the isotope-labeled carbon dioxide ($CO_2$) excreted in the expired air after oral administration of isotope-labeled $C_{12\text{-}38}$ fatty acid and the behavior of the abundance of the carbon dioxide contained in the expired air (the ratio of labeled $CO_2$ amount to unlabeled $CO_2$ amount, or the ratio of labeled $CO_2$ amount to total $CO_2$ amount), the abundance being calculated from the amount of isotope-labeled carbon dioxide ($CO_2$) excreted in the expired air. The present inventors further found that it is possible to perform a judgment as to whether a test subject has insulin resistance or hyperinsulinemia without insulin resistance, based on the measurement results obtained from the test subject.

The present inventors also confirmed that the sugar/fatty acid combustion ratio in a test subject can be measured with high accuracy by combining a result of a breath test using isotope-labeled $C_{12\text{-}38}$ fatty acid with the result of a breath test using isotope-label glucose or a blood glucose level, and that insulin resistance in a test subject can also be measured from the sugar/fatty acid combustion ratio with high accuracy.

The present invention has been accomplished based on these findings, and includes the following embodiments:
(1) Method for Measuring Insulin Resistance
(1-1) A method for measuring insulin resistance of a test subject, comprising steps (a) and (b) below:

(a) intravenously administering a composition to a test subject and collecting expired air, the composition comprising, as an active ingredient, a $C_{12\text{-}38}$ fatty acid or a salt thereof labeled with at least one isotope of C, wherein the $C_{12\text{-}38}$ fatty acid or a salt thereof is converted in the body into labeled carbon dioxide that is excreted in expired air; and
(b) determining the ratio of labeled $CO_2$ amount to unlabeled $CO_2$ amount contained in the expired air or the ratio of labeled $CO_2$ amount to total $CO_2$ amount contained in the expired air.

As described below, step (b) can be performed by determining, for example, $\Delta\%$ $^{13}C$ (amount of change in $^{13}C$ concentration: atom %) or $\Delta^{13}C$ value (amount of change in $\delta^{13}C$ value: ‰).

(1-2) The method for measuring insulin resistance according to (1-1), further comprising step (c) below:
(c) comparing "the ratio of labeled $CO_2$ amount to unlabeled $CO_2$ amount contained in the expired air or the ratio of labeled $CO_2$ amount to total $CO_2$ amount contained in the expired air" obtained from the test subject in step (b) (test subject value) with "the ratio of labeled $CO_2$ amount to unlabeled $CO_2$ amount contained in the expired air or the ratio of labeled $CO_2$ amount to total $CO_2$ amount contained in the expired air" of a healthy subject (control value), and determining that the insulin sensitivity of the test subject is decreased (insulin resistance) when the test subject value is higher than the control value, and that the insulin sensitivity of the test subject is normal or not decreased when the test subject value is equivalent to or lower than the control value.

(1-3) The method for measuring insulin resistance according to (1-1), wherein the test subject is a hyperinsulinemia patient, the method further comprising step (d) below:
(d) comparing "the ratio of labeled $CO_2$ amount to unlabeled $CO_2$ amount contained in the expired air or the ratio of labeled $CO_2$ amount to total $CO_2$ amount contained in the expired air" obtained from the test subject in step (b) (test subject value) with "the ratio of labeled $CO_2$ amount to unlabeled $CO_2$ amount contained in the expired air or the ratio of labeled $CO_2$ amount to total $CO_2$ amount contained in the expired air" of a healthy subject (control value), and determining that the test subject has "insulin-nonresistant hyperinsulinemia" in which the insulin sensitivity is normal or not decreased when the test subject value is lower than the control value.

(1-4) The method for measuring insulin resistance according to (1-1), wherein the test subject is a hyperinsulinemia patient, the method further comprising step (e) below:
(e) comparing "the ratio of labeled $CO_2$ amount to unlabeled $CO_2$ amount contained in the expired air or the ratio of labeled $CO_2$ amount to total $CO_2$ amount contained in the expired air" obtained from the test subject in step (b) (test subject value) with "the ratio of labeled $CO_2$ amount to unlabeled $CO_2$ amount contained in the expired air or the ratio of labeled $CO_2$ amount to total $CO_2$ amount contained in the expired air" of a healthy subject (control value), and determining that the insulin sensitivity of the test subject is decreased, in other words, the test subject has "insulin resistance" or "Insulin-resistant hyperinsulinemia" when the test subject value is higher than the control value, and determining that the insulin sensitivity of the test subject is normal or not decreased, in other words, the test subject has "insulin-nonresistant hyperinsulinemia" when the test subject value is lower than the control value.

(1-5) The method for measuring insulin resistance according to any one of (1-1) to (1-4), wherein the isotope is $^{13}C$.

(1-6) The method for measuring insulin resistance according to any one of (1-1) to (1-5), wherein the $C_{12-38}$ fatty acid is a $C_{12-28}$ medium-chain, long-chain, or very-long-chain fatty acid.

(1-7) The method for measuring insulin resistance according to any one of (1-1) to (1-6), wherein the $C_{12-38}$ fatty acid is at least one member selected from the group consisting of lauric acid, myristic acid, pentadecylic acid, stearic acid, oleic acid, and palmitic acid.

(1-8) The method for measuring insulin resistance according to any one of (1-1) to (1-7), wherein the $C_{12-38}$ fatty acid labeled with at least one Isotope C is 1-$^{13}$C-palmitic acid, 1-$^{13}$C-stearic acid, or 1-$^{13}$C-oleic acid wherein the carbon at the 1-position is labeled with $^{13}$C.

(1-9) The method for measuring insulin resistance according to any one of (1-1) to (1-8), wherein step (a) is performed with a test subject in a feeding state (non-fasting state).

(1-10) The method for measuring insulin resistance according to any one of (1-1) to (1-9), wherein the method detects the presence or absence of insulin resistance of a hyperinsulinemia test subject.

(1-11) The method for measuring insulin resistance according to any one of (1-1) to (1-10), wherein the test subject has at least one condition selected from the group consisting of borderline diabetes, type II diabetes, and liver disease (liver cirrhosis, NASH, NAFLD).

(2) The Method for Measuring Sugar/Fatty Acid Combustion Ratio (2-1) A method for measuring a sugar/fatty acid combustion ratio in a test subject, using, as an index, a value ($AUC_t$ [labeled C-glucose]/$AUC_t$[labeled C-fatty acid]) determined by dividing [an area under the Δ-labeled C(‰)-expired air collection time t curve] obtained by a glucose metabolism ability measurement method having steps (i) and (ii) below (hereinafter referred to as "$AUC_t$[labeled C-glucose]") by [an area under the Δ-labeled C(‰)-expired air collection time t curve] obtained by the method for measuring insulin resistance according to any one of (1-1) to (1-11) (hereinafter referred to as "$AUC_t$[labeled C-fatty acid]"):

(i) intravenously administering a composition to a test subject and collecting expired air, the composition comprising, as an active ingredient, glucose labeled with at least one isotope of C, wherein the glucose is converted in the body into labeled carbon dioxide that is excreted in expired air; and (ii) determining the ratio of labeled $CO_2$ amount to unlabeled $CO_2$ amount contained in the expired air or the ratio of labeled $CO_2$ amount to total $CO_2$ amount contained in the expired air.

(2-2) A method for measuring a sugar/fatty acid combustion ratio in a test subject body, using, as an index, a value (1/blood glucose level/$AUC_t$[labeled C-fatty acid]) determined by dividing the reciprocal of a blood glucose level (1/blood glucose level) of the test subject by [an area under the Δ-labeled C(‰)-expired air collection time t curve] obtained by the method for measuring insulin resistance according to any one of (1-1) to (1-11) (hereinafter referred to as "$AUC_t$[labeled C-fatty acid]").

(2-3) A method for measuring a sugar/fatty acid combustion ratio in a test subject body using a value ([1/blood glucose level]/Ct[labeled C-fatty acid] (t=1-30 min)) determined by dividing the reciprocal of a blood glucose level (1/blood glucose level) of the test subject by Ct[labeled C-fatty acid] (t=1-30 min) of Δ-labeled C(‰) obtained by the method for measuring insulin resistance according to any one of (1-1) to (1-11).

(2-4) The method for measuring a sugar/fatty acid combustion ratio according to any one of (2-1) to (2-3), wherein the test subject is in a fasting state or a feeding state (non-fasting state).

(3) Composition for Measuring Insulin Resistance (3-1) A composition in an injectable dosage form for measuring insulin resistance, the composition comprising, as an active ingredient, a $C_{12-38}$ fatty acid or a salt thereof labeled with at least one isotope of C, wherein the $C_{12-38}$ fatty acid or a salt thereof is converted in the body into labeled carbon dioxide that is excreted in expired air.

(3-2) The composition for measuring insulin resistance according to (3-1), wherein the isotope is $^{13}$C.

(3-3) The composition for measuring insulin resistance according to (3-1) or (3-2), wherein the $C_{12-38}$ fatty acid is a $C_{12-38}$ saturated fatty acid or a $C_{18}$ unsaturated fatty acid.

(3-4) The composition for measuring insulin resistance according to any one of (3-1) to (3-3), wherein the $C_{12-38}$ fatty acid is at least one member selected from the group consisting of lauric acid, myristic acid, pentadecylic acid, stearic acid, oleic acid, and palmitic acid.

(3-5) The composition for measuring insulin resistance according to any one of (3-1) to (3-4), wherein the $C_{12-38}$ fatty acid labeled with at least one Isotope C is 1-$^{13}$C-palmitic acid, 1-$^{13}$C-stearic acid, or 1-$^{13}$C-oleic acid wherein the carbon at the 1-position is labeled with $^{13}$C.

(4) Use of Labeled C-Fatty Acid (4-1) Use of a composition in an injectable dosage form for a breath test for measuring insulin resistance, the composition comprising, as an active ingredient, a $C_{12-38}$ fatty acid labeled with at least one isotope of C, wherein the $C_{12-38}$ fatty acid is converted in the body into labeled carbon dioxide that is excreted in expired air.

(4-2) The use of (4-1), wherein the composition is the composition for measuring insulin resistance according to any one of (3-1) to (3-5).

(4-3) Use of a composition in an injectable dosage form for a breath test for 1.5 measuring a sugar/fatty acid combustion ratio, the composition comprising, as an active ingredient, a $C_{12-38}$ fatty acid labeled with at least one isotope of C, wherein the $C_{12-38}$ fatty acid is converted in the body into labeled carbon dioxide that is excreted in expired air (4-4) The use according to (4-3), wherein the composition is the composition for measuring insulin resistance according to any one of (3-1) to (3-5).

Advantageous Effects of Invention

The method of the present invention makes it possible to measure and evaluate insulin resistance in a test subject rapidly and with high accuracy. The accuracy and rapidity can be further improved by performing the method of the present invention on a test subject under feeding conditions. Further, the method of the present invention makes it possible to measure and evaluate low sensitivity to insulin (insulin resistance) of a test subject in a short period of time, i.e., within 60 minutes, preferably within 30 minutes, more preferably within 15 minutes. Therefore, the method of the present invention makes it unnecessary to restrain a test subject for a long period of time, thereby eliminating the test subject's physical or mental burden when measuring the insulin resistance of the test subject.

Further, the method of the present invention makes it possible to measure the presence or absence of insulin resistance in a hyperinsulinemia test subject, and enable discrimination between insulin-resistant hyperinsulinemia and insulin-nonresistant hyperinsulinemia. The insulin-nonresistant hyperinsulinemia is a pre-insulin-resistant (low sensitivity to insulin) state; thus, a test subject determined to be in an insulin-nonresistant hyperinsulinemia state can be prevented from developing an insulin-resistant condition through diet and exercise.

Further, the present invention makes it possible to not only measure the insulin resistance of hyperinsulinemia patients such as borderline diabetes or type II diabetes patients, but also measure the insulin resistance of liver disease (liver cirrhosis, NASH (non-alcoholic steatohepatitis), NAFLD (non-alcoholic fatty liver disease), etc.) patients.

Further, by combining a breath test using an isotope-labeled $C_{12-38}$ fatty acid and a breath test using isotope-labeled glucose, it is possible to measure sugar/fatty acid combustion ratio in a test subject. This method enables measurement as to whether the test subject uses sugar or fatty acid as the energy source in place of, and more sensitively than, respiratory quotient. Further, the insulin resistance in a test subject can also be evaluated with high accuracy from the "sugar/fatty acid combustion ratio" obtained by the method of the present invention.

BRIEF DESCRIPTION OF DRAWINGS

FIG. 2(A) shows the results of Lean rats (fasting: -♦-, feeding: -◇-), and FIG. 2(B) shows the results of Fatty rats (fasting: -♦-, feeding: -□-). The ordinate axis denotes $\Delta^{13}C(‰)$ in the expired air, and the abscissa axis denotes expired air collection time (t minutes) after the administration of U-$^{13}C$-glucose solution (Experimental Example 2).

FIG. 3(A) shows the results of Lean rats (fasting: -♦-, feeding: -◇-), and FIG. 3(B) shows the results of Fatty rats (fasting: -■-, feeding: -□-). The ordinate axis denotes $\Delta^{13}C(‰)$ in the expired air, and the abscissa axis denotes expired air collection time (t minutes) after the administration of $1$-$^{13}C$-sodium acetate solution (Experimental Example 2).

FIG. 4(A) shows the results of Lean rats (fasting: -♦-, feeding: -◇-), and FIG. 4(B) shows the results of Fatty rats (fasting: -■-, feeding: -□-). The ordinate axis denotes $\Delta^{13}C(‰)$ in the expired air, and the abscissa axis denotes expired air collection time (t minutes) after the administration of $1$-$^{13}C$-sodium octanoate solution (Experimental Example 2).

FIG. 5(A) shows the results of Lean rats (fasting: -♦-, feeding: -◇-), and FIG. 5(B) shows the results of Fatty rats (fasting: -■-, feeding: -□-). The ordinate axis denotes $\Delta^{13}C(‰)$ in the expired air, and the abscissa axis denotes expired air collection time (t minutes) after the administration of $1$-$^{13}C$-lauric acid solution (Experimental Example 2).

FIG. 6(A) shows the results of Lean rats (fasting: -♦-, feeding: -◇-), and FIG. 6(B) shows the results of Fatty rats (fasting: -♦-, feeding: -□-). The ordinate axis denotes $\Delta^{13}C(‰)$ in the expired air, and the abscissa axis denotes expired air collection time (t minutes) after the administration of $1$-$^{13}C$-sodium palmitate solution (Experimental Example 2).

FIG. 7(A) shows the results of Lean rats (fasting: -♦-, feeding: -◇-), and FIG. 7(B) shows the results of Fatty rats (fasting: -■-, feeding: -□-). The ordinate axis denotes $\Delta^{13}C(‰)$ in the expired air, and the abscissa axis denotes expired air collection time (t minutes) after the administration of $1$-$^{13}C$-oleic acid solution (Experimental Example 2).

FIG. 8(A) denotes the results of LETO rats (fasting: -♦-, feeding: -◇-), and FIG. 8(B) denotes the results of OLETF rats (fasting: -■-, feeding: -□-). The ordinate axis denotes $\Delta^{13}C(‰)$ in the expired air, and the abscissa axis denotes expired air collection time (t minutes) after the administration of $1$-$^{13}C$-sodium palmitate solution (Experimental Example 3).

In FIGS. 9(A) and 9(B), the ordinate axis denotes $\Delta^{13}C(‰)$ in the expired air, and the abscissa axis denotes expired air collection time (t minutes) after the administration of $1$-$^{13}C$-sodium palmitate solution (Experimental Example 3).

In FIGS. 10(A) and 10(B), the ordinate axis denotes $\Delta^{13}C(‰)$ in the expired air, and the abscissa axis denotes expired air collection time (t minutes) after the administration of $1$-$^{13}C$-sodium palmitate solution (Experimental Example 3).

In FIGS. 11(A) and 11(B), the ordinate axis denotes $\Delta^{13}C(‰)$ in the expired air, and the abscissa axis denotes expired air collection time (t minutes) after the administration of $1$-$^{13}C$-sodium palmitate solution (Experimental Example 4).

In FIGS. 12(A) and 12(B), the ordinate axis denotes $\Delta^{13}C(‰)$ in the expired air, and the abscissa axis denotes expired air collection time (t minutes) after the administration of 1-$^{13}$C-sodium palmitate solution (Experimental Example 4).

Figure 1:
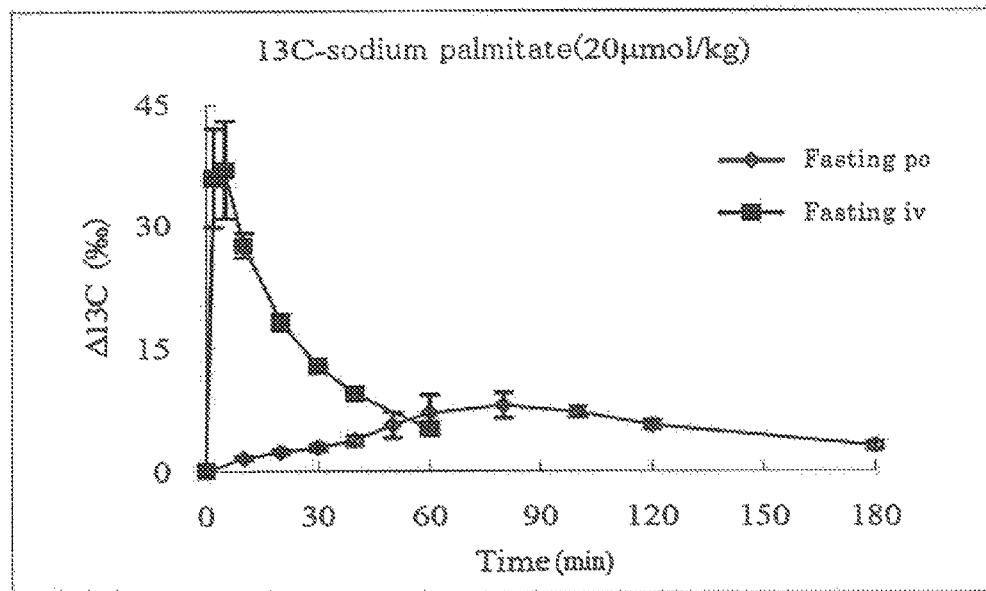
FIG. 1 shows transition of $\Delta^{13}C(‰)$ in the expired air measured after oral administration (po) (-◇-) or intravenous injection (iv) (-■-) of a $1$-$^{13}C$-sodium palmitate solution into fasted Zucker rats. The ordinate axis denotes $\Delta^{13}C(‰)$ in the expired air, and the abscissa axis denotes measurement time (t minutes) after the administration of $1$-$^{13}C$-sodium palmitate (Experimental Example 1).

DESCRIPTION OF EMBODIMENTS (I) Description of Terms and Analysis Methods Relating to Labeled C-Breath Test The method for measuring insulin resistance and sugar/fatty acid combustion ratio of the present invention is based on using a labeled C-breath test, such as a $^{13}$C-breath test. Thus, before description of the present invention, terms and analysis methods thereof relating to a labeled C-breath test are described.

Here, $^{13}$C is described as an example of "Isotope C" used in the present invention.

(1) $\delta^{13}C$ Value (‰)

Abundances of isotopes are expressed in terms of isotopic ratio (R) in which the most abundant isotope of the same element is used as the denominator. Thus, with respect to carbon 13 ($^{13}$C), R value is expressed by the following formula in which carbon 12 ($^{12}$C) is used as the denominator.

$$R = {}^{13}C/{}^{12}C \quad \text{(Formula 1)}$$

Since R is a very small numerical value, it is difficult to directly measure. When a mass spectrometer is used for more accurate quantification, comparison with a standard substance is always performed. The measurement result is represented by δ value defined by the following formula.

$$\delta^{13}C = ([R_{SAM}/R_{STD}] - 1) \times 1000 \quad \text{(Formula 2)}$$

$\delta^{13}C$: $\delta^{13}C$ value (‰)
$R_{SAM}$: abundance of $^{13}$C in sample gas
$R_{STD}$: abundance of $^{13}$C in standard gas When carbon dioxide derived from limestone (PDB) is used as standard gas, $R_{STD}$ is $R_{PDB} = 0.0112372$.

(2) $\Delta^{13}C$ Value(‰)

"$\Delta^{13}C$ value(‰)" means a value ($\Delta^{13}C$) obtained by subtracting the $\delta^{13}C$ value before administration of a reagent (i.e., naturally occurring δ value of $^{13}$C) as a background from the $\delta^{13}C$ value after administration of the reagent, as shown in the following formula.

$$\Delta^{13}C(‰) = ({}^{13}C)_t - (\delta^{13}C)_0 \quad \text{(Formula 3)}$$

$\Delta^{13}C$: amount of change in $\delta^{13}C$ value (‰)
$(\delta^{13}C)_t$: $\delta^{13}C$ value t hr. after reagent administration (‰)
$(\delta^{13}C)_0$: $\delta^{13}C$ value 0 hr. before reagent administration (‰)

(3) $^{13}$C Concentration in Expired Air (% $^{13}$C: Atom %)

The $^{13}$C concentration in expired air (% $^{13}$C: atom %) is defined by the following formula.

$$\%{}^{13}C = [{}^{13}C/({}^{13}C + {}^{12}C)] \times 100$$

To convert the relative value $\delta^{13}C$ defined in (1) into the $^{13}$C concentration (%) in the total carbon, which is a common concept of concentration, the following method can be used.

First, the numerator and denominator on the right side of the above formula are divided by $^{12}$C, and converted into R based on (Formula 1). The following formula is thus obtained.

$$\%{}^{13}C = [R/(R+1)] \times 100 \quad \text{(Formula 4)}$$

If $R_{SAM}$ obtained in (Formula 2) is substituted into R above and rearranged, the following formula is obtained. The $^{13}$C concentration (% $^{13}$C) can be expressed by using the $\Delta^{13}C$ value.

$$\%{}^{13}C = \{[(\delta^{13}C/10000) + 1] \times R_{PDB} \times 100\}/\{[[(\delta^{13}C/1000) + 1] \times R_{PDB}] + 1\} \quad \text{(Formula 5)}$$

% $^{13}$C: $^{13}$C concentration (atom %)
$\delta^{13}C$: $\delta^{13}C$ value(‰)
$R_{PDB}$: abundance of $^{13}$C in PDB standard gas=0.0112372

(4) Amount of Change in $^{13}$C Concentration ($\Delta\%$ $^{13}$C)

As defined in the following formula, the amount of change in $^{13}$C concentration (% $^{13}$C) in expired air ($\Delta\%$ $^{13}$C) is determined by subtracting the $^{13}$C concentration 0 hr. before administration [(% $^{13}$C)$_0$] from the $^{13}$C concentration t hr. after administration [(% $^{13}$C)].

$$\Delta\%{}^{13}C = (\%{}^{13}C)_t - (\%{}^{13}C)_0 \quad \text{(Formula 6)}$$

$\Delta\%$ $^{13}$C: amount of change in $^{13}$C concentration (atom %)
(% $^{13}$C)$_t$: $^{13}$C concentration t hr. after reagent administration (atom %)
(% $^{13}$C)$_0$: $^{13}$C concentration 0 hr. before reagent administration (atom %)

(5) Relation Between $\Delta^{13}C$ Value (‰) and Amount of Change in $^{13}$C Concentration ($\Delta\%$ $^{13}$C)

The natural abundance (R) of $^{13}$C is about 0.011, and even when a labeled reagent is administered, the increased amount in expired air is only about +0.001 to 0.002. Thus, the natural abundance can be regarded as R→0, and (Formula 4), which expresses % $^{13}C$ by using R, can be approximated by the following formula.

$$\%^{13}C=[R/(R+1)]\times100-R\times100$$

Using this approximate expression, an approximation that determines the $^{13}C$ concentration (Formula 7) can be obtained as follows: first, $R_{SAM}$ is determined by (Formula 2), which defines $\delta^{13}C$, substituted into R in the above formula, and rearranged.

$$\%^{13}C=[(\delta^{13}C/1000)+1]\times R_{PDB}\times100 \quad \text{(Formula 7)}$$

When this is substituted into (Formula 6), $\Delta\%$ $^{13}C$ can be calculated from $\Delta^{13}C$, as shown in (Formula 8) below.

$$\begin{aligned}\Delta\%\,^{13}C &= (\%\,^{13}C)_t - (\%\,^{13}C)_0 \quad \text{(Formula 8)}\\ &= \{[(\delta^{13}C)_t - (\delta^{13}C)_0]/1000\}\times R_{PDB}\times100\\ &= (\Delta^{13}C\times R_{PDB})/10\end{aligned}$$

$\Delta\%$ $^{13}C$: amount of change in $^{13}C$ concentration (atom %)
$\Delta^{13}C$: amount of change in $\delta^{13}C$ value (‰)
$R_{PDB}$: abundance of $^{13}C$ in PDB standard gas=0.0112372
(II) Composition for Measuring Insulin Resistance The composition for measuring insulin resistance of the present invention comprises, as an active ingredient, a $C_{12-38}$ fatty acid or a salt thereof labeled with at least one isotope of C, wherein the $C_{12-38}$ fatty acid or a salt thereof is converted in the body into labeled $CO_2$ gas that is excreted in expired air. The labeled C-fatty acid or a salt thereof used in the present invention has a feature such that, after being administered to a test subject, the labeled C-fatty acid or a salt thereof is metabolized according to lipid metabolism ability in the body and excreted in expired air in the form of carbon dioxide containing labeled C, which reflects the degree of lipid metabolism ability of the test subject.

As mentioned above, examples of fatty acid used in the present invention include $C_{12-38}$ fatty acids. Examples of such fatty acids include medium-chain fatty acids having 12 to less than 18 carbon atoms, long-chain fatty acids having 18 to less than 24 carbon atoms, very-long-chain fatty acids having 24 to 28 carbon atoms, and ultra-long-chain fatty acids having 30 to 38 carbon atoms. Preferably, the fatty acid is $C_{12-28}$ medium-, long-, or very-long-chain fatty acid, more preferably medium- or long-chain fatty acid having 12 to less than 24 carbon atoms. More specifically, examples include lauric acid (C12), myristic acid (C14), pentadecylic acid (C15), palmitic acid (C16), stearic acid (C18), arachidic acid and like saturated fatty acids; palmitoleic acid (C16), oleic acid (C18), vaccenic acid (C18), nervonic acid (C24) and like unsaturated fatty acids having one double bond; linoleic acid (C18), 8,11-icosadienoic acid and like unsaturated fatty acids having two double bonds; linolenic acid (C18), arachidonic acid (C20) and like unsaturated fatty acids having three or more double bonds. Preferable examples include saturated fatty acids and unsaturated fatty acids having one double bond; among them, lauric acid (C12:0), stearic acid (C18:0), palmitic acid (C16:0), and oleic acid (C18:1) are preferable. Stearic acid (C18) and palmitic acid (C16) are more preferable.

There is no particular limitation on isotopes used in labeling carbon atoms of fatty acid, and specific examples include $^{13}C$, and $^{14}C$. Such isotopes may be radioactive or non-radioactive; however, from the standpoint of safety, non-radioactive isotopes are preferable. For example, $^{13}C$ is desirable for use as such an isotope.

The isotope-labeled fatty acid is labeled in such a manner that at least a portion of the $CO_2$ formed through the lipid metabolic pathway (fatty acid metabolic pathway) is isotope-labeled. Examples of such isotope-labeled fatty acid include compounds in which the carbon atom at the 1-position of fatty acid is labeled with an isotope. Specific examples include 1-$^{13}C$-labeled fatty acid. Fatty acid in which at least the carbon atom at the 1-position is isotope-labeled may be used; that is, in addition to the carbon atom at the 1-position, one or more of other carbon atoms or all of the carbon atoms may be isotope-labeled. There is no particular limitation on the method for labeling compounds such as fatty acid with isotopes such as $^{13}C$ or $^{14}C$, and a wide variety of commonly used methods may be employed (Sasaki, "5.1 Antei Doitai no Rinsho Shindan heno Oyo [5.1 Application of Stable Isotopes in Clinical Diagnosis]": Kagaku no Ryoiki [Journal of Japanese Chemistry]107, "Antei Doitai no I/Yakugaku Seibutsugaku heno Oyo [Application of Stable Isotopes in Medicine, Pharmacy, and Biology]," pp. 149-163 (1975), Nankodo: Kajiwara, RADIOISOTOPES, 41, 45-48 (1992), etc.). Such isotope-labeled compounds, particularly 1-$^{13}C$-labeled-lauric acid, 1-$^{13}C$-labeled-palmitic acid, 1-$^{13}C$-labeled-stearic acid, 1-$^{13}C$-labeled-oleic acid, and salts thereof described in the Examples, are commercially available as conveniently usable commercial products.

The salts of $C_{12-38}$ fatty acid may be any pharmaceutically acceptable salts that can be administered to living organisms. Examples thereof include sodium, potassium, or like alkali metal salt; and magnesium, calcium, or like alkaline-earth metal salt. Alkali metal salts are preferable. Sodium salt is particularly preferable.

There is no particular limitation on the composition of the present invention in terms of its form, components other than the labeled C-fatty acid, proportion of each component, preparation method of the composition, etc., as long as the labeled C-fatty acid is absorbed in the body after administration, and excreted in expired air in the form of labeled carbon dioxide after metabolism.

As indicated in Experimental Example 1 described later, the dosage forms are preferably injectable dosage forms, in particular, intravenous dosage forms from the standpoint of ensuring rapid rise of "$\Delta^{13}C$(‰)," i.e., high-speed excretion in the expired air as $^{13}CO_2$ after C-labeled fatty acid administration. Examples of injectable dosage forms include injections and drops (in liquid, suspension, or emulsion form).

The composition of the present invention may substantially consist of the labeled C-fatty acid, which is an active ingredient; however, as long as the functions and the effects of the present invention are not adversely affected, any pharmaceutically acceptable carriers and/or additives that are generally used in this field may be added as other components according to the pharmaceutical form (dosage form). In this case, there is no particular limitation on the amount of the labeled C-fatty acid contained as an active ingredient. For example, the amount of the labeled C-fatty acid is in the range of 1 to 99 wt % based on the total weight (100 wt %) of the composition, and is suitably controlled within this range.

More specifically, when the composition of the present invention is prepared into an injectable form such as liquid, suspension, or emulsion, for example, various carriers and/or additives suitable to such forms may be used in addition to purified water or distilled water for injection. Examples of additives include additives commonly used, such as tonicity-adjusting agents (e.g., sodium chloride etc.), pH adjusters (e.g., hydrochloric acid, sodium hydroxide, etc.), buffers (e.g., boric acid, sodium monohydrogen phosphate, sodium dihydrogen phosphate, etc.), preservatives (e.g., benzalkonium chloride etc.), and thickeners (e.g., carboxyvinyl polymers etc.). Insofar as the composition of the present invention can be made into an injectable form when used, it may have a solid form, such as a freeze-dried preparation or a spray-dried preparation, that is to be dissolved in distilled water for injection or the like when used.

In the measurement method described later, the composition of the present invention is used as an administration sample (test sample) to be administered to a test subject. More specifically, the composition of the present invention is used as a test sample to be administered to a test subject to measure insulin resistance in the test subject, or as a test sample to be administered to a test subject to measure a sugar/fatty acid combustion ratio in the test subject.

All of these measurement methods are performed by intravenously administering the composition of the present invention to a test subject (including a human and an animal), collecting expired air, measuring the abundance of carbon dioxide contained in the expired air (the ratio of labeled $CO_2$ amount to unlabeled $CO_2$ amount or the ratio of labeled $CO_2$ amount to total $CO_2$ amount), and using the abundance as an index. The details are described in (III) below.

The amount of the labeled C-fatty acid (active ingredient) contained in the composition for measuring insulin resistance of the present invention may be suitably selected according to each case. More specifically, the dose may be adjusted so that the amount of the labeled C-fatty acid (active ingredient) per dose is in the range of 5 mg/body to 50 g/body, and preferably 10 mg/body to 25 g/body.

(III) Method for Measuring Insulin Resistance

Use of the above-described composition for measuring insulin resistance of the present invention enables measurement of low sensitivity to insulin (insulin resistance) in a test subject (a human, or a mammal other than humans).

As described below, the measurement of insulin resistance can basically be performed through the step of administering the above composition, which comprises the labeled C-fatty acid as an active ingredient, to a mammal including a human (test subject), and collecting expired air ([step (a)] of the method of the present invention), and the step of measuring the abundance of carbon dioxide contained in the expired air (the ratio of labeled $CO_2$ amount to unlabeled $CO_2$ amount or the ratio of labeled $CO_2$ amount to total $CO_2$ amount) ([step (b)] of the method of the present invention).

[Step (a)] The step of administering a composition to a test subject and collecting expired air, the composition comprising, as an active ingredient, a $C_{12-38}$ fatty acid or a salt thereof labeled with at least one isotope of C, wherein the $C_{12-38}$ fatty acid or a salt thereof is converted in the body into labeled carbon dioxide that is excreted in expired air (hereunder such fatty acid and a salt thereof are collectively referred to as a "labeled C-fatty acid" unless otherwise specified); and

[Step (b)] The step of determining the ratio of labeled $CO_2$ amount to unlabeled $CO_2$ amount contained in the expired air or the ratio of labeled $CO_2$ amount to total $CO_2$ amount contained in the expired air.

As described above, the labeled C-fatty acid used in the present invention has a feature such that, after being intravenously administered to a test subject, the labeled C-fatty acid is metabolized according to fatty acid metabolism ability of the test subject and excreted in expired air in the form of "carbon dioxide containing labeled C," which reflects the degree of the fatty acid metabolism ability.

As indicated in Experimental Example 1, administration of the composition of the present invention, which comprises the labeled C-fatty acid as an active ingredient, is preferably performed through intravenous administration in terms of high accuracy.

The amount of the labeled C-fatty acid (active ingredient) contained in the composition for measuring insulin resistance of the present invention may be suitably selected according to each case (individual difference of test subject, condition of the test subject such as whether the test subject is in a fasting state or a feeding state, etc.). The dose of one intravenous administration is adjusted so that the amount of the labeled C-fatty acid (active ingredient) therein is in the range of 5 mg/body to 50 g/body, and preferably 10 mg/body to 25 g/body.

As described above, the target test subjects of the present invention are humans, or mammals other than humans. Examples of mammals other than humans include mice, rats, guinea pigs, rabbits, dogs, cats, monkeys, pigs, cattle, horses, and the like. The mammals other than humans are preferably test animals such as mice, rats, guinea pigs, rabbits, dogs, and monkeys.

The test subject may be in a fasting state or feeding state before being subjected to step (a). As indicated in Experimental Example 2 described later, when a test subject in a feeding state, rather than a test subject in a fasting state, is subjected to step (a), "the ratio of labeled $CO_2$ amount to unlabeled $CO_2$ amount or the ratio of labeled $CO_2$ amount to total $CO_2$ amount" can be measured in step (b) with high accuracy for a short period of time. Thus, a test subject in a feeding state is preferable.

The case in which a composition comprising $^{13}$C-labeled fatty acid as an active ingredient is used (i.e., the case in which the labeled $CO_2$ measured is $^{13}CO_2$) is described below as an example of the method for measuring insulin resistance of a test subject based on the abundance of carbon dioxide contained in expired air (the ratio of labeled $CO_2$ amount to unlabeled $CO_2$ amount or the ratio of labeled $CO_2$ amount to total $CO_2$ amount) determined in step (b) using the expired air collected in step (a).

(1) The abundance of carbon dioxide contained in the collected expired air (the ratio of $^{13}CO_2$ amount to total $CO_2$ amount) is calculated according to the below-described method as the amount of change in $^{13}$C concentration ($\Delta\%$ $^{13}$C), which is obtained by subtracting the $^{13}$C concentration (atom %) [(% $^{13}$C)$_0$] before administration of $^{13}$C-labeled fatty acid.

The $^{13}$C concentration (atom %) in total carbon contained in expired air [$^{13}$C concentration (% $^{13}$C) in expired air (% $^{13}$C)] is determined; further, the $^{13}$C concentration (atom %) before administration of the $^{13}$C-labeled compound [(% $^{13}$C)$_0$] is subtracted according to Formula 6, thereby obtaining the amount of change in the $^{13}$C concentration ($\Delta\%$ $^{13}$C).

$$^{13}C \text{ concentration (atom \%)} = [^{13}C/(^{13}C+^{12}C)] \times 100$$

$$\Delta\%^{13}C = (\%^{13}C)_t - (\%^{13}C)_0 \quad \text{(Formula 6)}$$

$\Delta\%$ $^{13}$C: amount of change in $^{13}$C concentration (atom %)
(% $^{13}$C)$_t$: $^{13}$C concentration t hr. after reagent administration (atom %)
(% $^{13}$C)$_0$: $^{13}$C concentration 0 hr. before reagent administration (atom %)

(2) If necessary, the amount of change in the $^{13}$C concentration ($\Delta\%$ $^{13}$C) may be converted into $\Delta^{13}$C value (‰) [amount of change in $\delta^{13}$C value (‰) or DOB(‰)] based on Formula 5 and Formula 3.

$$\%\ ^{13}C = \{[(\delta^{13}C/1000)+1] \times R_{PDB} \times 100\}/\{[[(\delta^{13}C/100)+1] \times R_{PDB}]+1\} \quad \text{(Formula 5)}$$

% $^{13}C$: $^{13}C$ concentration (atom %)
$\delta^{13}C$: $\delta^{13}C$ value (‰)
$R_{PDB}$: abundance of $^{13}C$ in PDB standard gas=0.0112372

$$\Delta^{13}C(‰)=(^{13}C)_t-(\delta^{13}C)_0 \quad \text{(Formula 3)}$$

$\Delta^{13}C(‰)$: amount of change in $\delta^{13}C$ value (‰)
$(\delta^{13}C)$: $\delta^{13}C$ value t hr. after reagent administration (‰)
$(\delta^{13}C)_0$: $\delta^{13}C$ value 0 hr. before reagent administration (‰)

The concentration of labeled C excreted in expired air after the composition for measuring insulin resistance, which comprises the labeled C-fatty acid as an active ingredient, is administered, or the corresponding $\Delta\%$ $^{13}C$ (atom %) or $\Delta^{13}C$ value(‰) reflect insulin resistance in a test subject, as indicated in the Experimental Examples described later. The method of the present invention, which uses the composition, allows insulin resistance in a test subject to be measured rapidly and with high accuracy.

The measurement and analysis of the labeled carbon dioxide contained in the expired air sample vary depending on whether the isotope used is radioactive or non-radioactive. However, the measurement and analysis may be performed by a commonly used analysis method, such as the liquid scintillation counter method, mass spectrometry, infrared spectroscopy, emission spectrometry, or the magnetic resonance spectrum method. From the viewpoint of measurement accuracy, infrared spectroscopy and mass spectrometry are preferable.

Insulin resistance in a test subject can be determined by the following method, using, as an index, "the ratio of labeled $CO_2$ amount to unlabeled $CO_2$ amount contained in the expired air or the ratio of labeled $CO_2$ amount to total $CO_2$ amount contained in the expired air" ($\Delta\%$ $^{13}C$(atom %) or $\Delta^{13}C$ value(‰)) obtained in step (b) described above.

(c-1) "The ratio of labeled $CO_2$ amount to unlabeled $CO_2$ amount contained in the expired air or the ratio of labeled $CO_2$ amount to total $CO_2$ amount contained in the expired air" ($\Delta\%$ $^{13}C$(atom %)) or $\Delta^{13}C$ value(‰)) obtained in the test subject in step (b) (test subject value) is compared with "the corresponding ratio of labeled $CO_2$ amount to unlabeled $CO_2$ amount contained in the expired air or the corresponding ratio of labeled $CO_2$ amount to total $CO_2$ amount contained in the expired air" ($\Delta\%$ $^{13}C$(atom %) or $\Delta^{13}C$ value(‰)) of a healthy subject (control value).

(c-2) As a result of the comparison, when the test subject value is higher than the control value, it is determined that the sensitivity to insulin of the test subject is decreased, more specifically, that the test subject is "insulin-resistant." If the test subject value is equal to or lower than the control value, it is determined that the sensitivity to insulin of the test subject is normal or not decreased.

Here, the healthy subject means a subject with healthy (normal) sensitivity to insulin. More specifically, the healthy subject does not have any abnormality in insulin secretion, and does not have glucose metabolic disorder (including hyperinsulinemia) such as diabetes (including type II diabetes and gestational diabetes), borderline diabetes, or liver disease (liver cirrhosis, NASH, NAFLD, etc.).

Using known or conventional diagnosis methods (blood glucose level measurement such as a 75 g glucose tolerance test, insulin resistance test, hemoglobin A1c, etc.) in the field, it is possible to determine whether the test subject is a healthy subject or not. For example, in the 75 g glucose tolerance test, glucose metabolism ability is determined to be normal when the blood glucose level on an empty stomach Is less than 110 mg/dl, and the blood glucose level two hours after glucose was loaded is less than 140 mg/dl.

Figure 2:
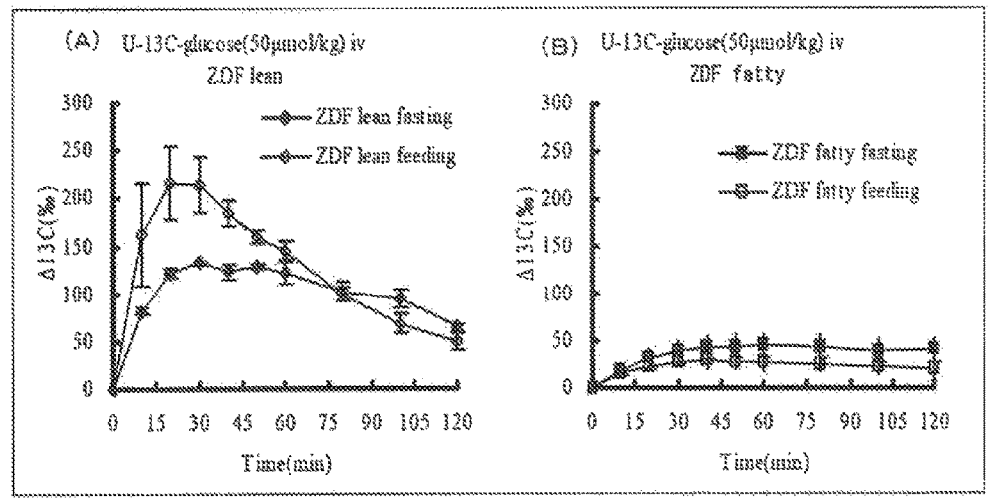
FIG. 2 shows transition of $\Delta^{3}C(‰)$ in the expired air measured after intravenous injection of a U-$^{13}C$-glucose solution to ZDF rats in a fasting or feeding state (Lean and Fatty).

As shown in Experimental Example 2 (FIG. 2), the glucose metabolism ability of a test subject model (insulin-resistant test subject) (ZDF Fatty in FIG. 2) who has developed diabetes or in a prediabetic stage is lower than that of a healthy subject (ZDF Lean in FIG. 2). By administering labeled C-fatty acid to the test subject model and performing step (b), as shown in FIG. 6(B) (a figure concerning ZDF Fatty), "the ratio of labeled $CO_2$ amount to unlabeled $CO_2$ amount contained in the expired air or the ratio of labeled $CO_2$ amount to total $CO_2$ amount contained in the expired air ($\Delta\%$ $^{13}C$(atom %) or $\Delta^{13}C$ value(‰))(test subject value) determined in step (b) is generally higher (increased) both in the fasting state and the feeding state than "the ratio of labeled $CO_2$ amount to unlabeled $CO_2$ amount contained in the expired air or the ratio of labeled $CO_2$ amount to total $CO_2$ amount contained in the expired air" ($\Delta\%$ $^{13}C$(atom %) or $\Delta^{13}C$ value(‰)) in a healthy subject (control value) (FIG. 6(A) (a figure regarding ZDF Lean)) (Experimental Example 2). Similar results were obtained in an experiment using OLETF rats as experimental animals instead of ZDF Fatty rats (see Experimental Example 3, FIG. 7). OLETF rat is a Type II diabetes model animal that develops diabetes accompanied by obesity or/and fatty liver, and diabetes complication. The difference in rise (increase) in h % $^{13}C$(atom %) or $\Delta^{13}C$ value(‰) of the insulin-resistant test subject with respect to the healthy subject Is more significant in the feeding state (see Experimental Example 3, comparison between FIGS. 8(A) and 8(B), and comparison between FIGS. 9(A) and 9(B)). This shows that the fatty acid metabolism ability of a test subject (insulin-resistant test subject), who developed diabetes or is in a prediabetic stage and has low insulin sensitivity, is higher (increased) than that of a healthy subject. Therefore, the method of the present invention makes it possible to indirectly measure insulin resistance in a test subject from fatty acid metabolism ability of the test subject. As is evident from FIGS. 8(B) and 9(B) showing experiment results in a feeding state, this method of the present invention is characterized in the clear difference between the value ($\Delta\%$ $^{13}C$ (atom %) or $\Delta^{13}C$ value(‰)) obtained from a test subject with low insulin sensitivity and the control value obtained from a healthy subject, and the highly accurate results that can be obtained shortly after the expired air collection (within 1 to 30 minutes, preferably within 1 to 15 minutes).

Figure 10:
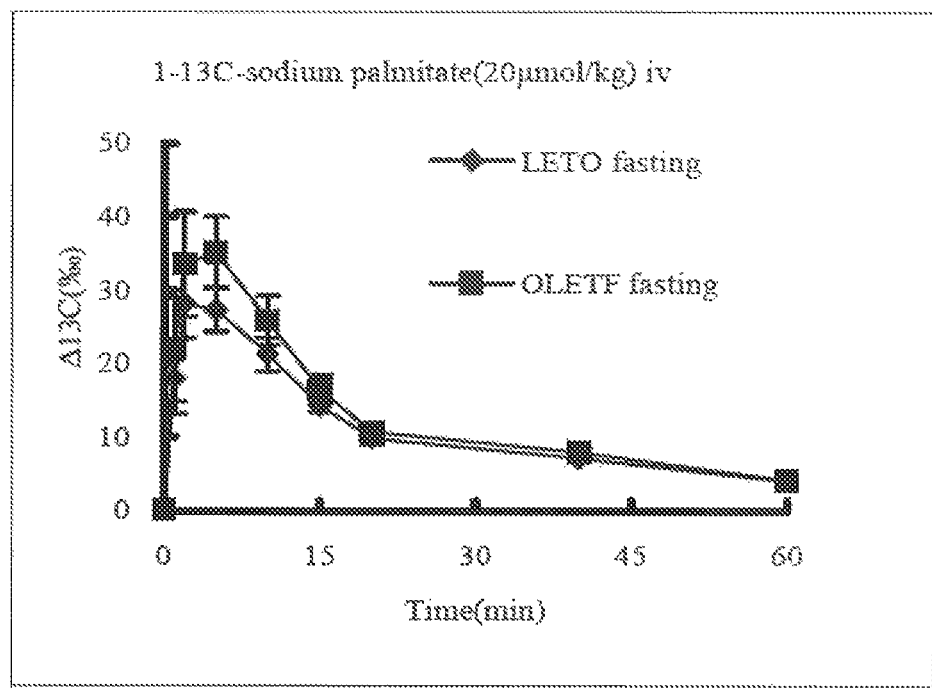
FIG. 10(A) shows transition of $\Delta^{13}C(‰)$ in the expired air measured after intravenous injection of a $1$-$^{13}C$-sodium palmitate solution to LETO rats (-♦-) and OLETF rats (-■-) in a fasting state.
FIG. 10(B) shows transition of $\Delta^{13}C(‰)$ in the expired air measured after intravenous injection of a $1$-$^{13}C$-sodium palmitate solution to LETO rats (-◇-) and OLETF rat (-□-) in a feeding state.
Figure 10:
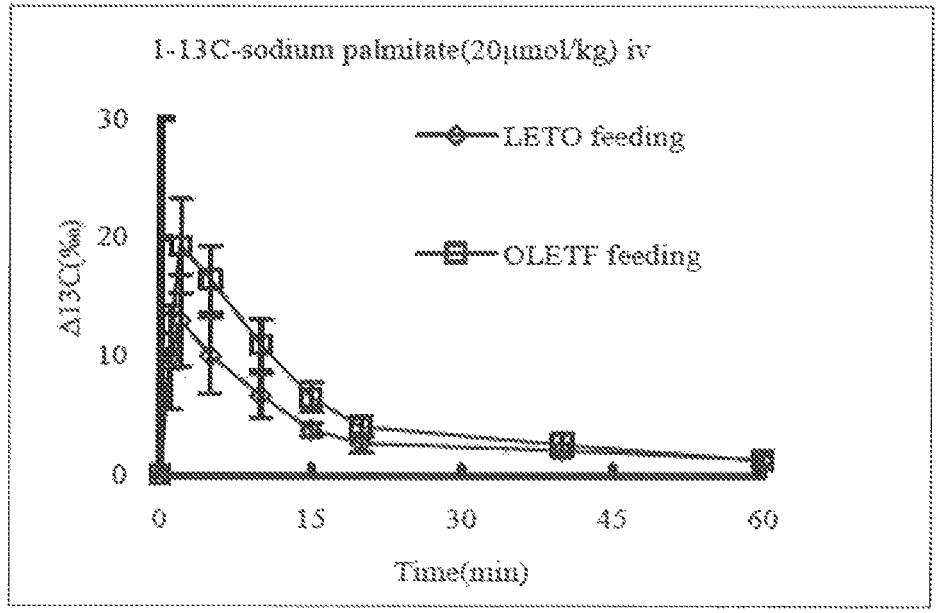
Figure 11:
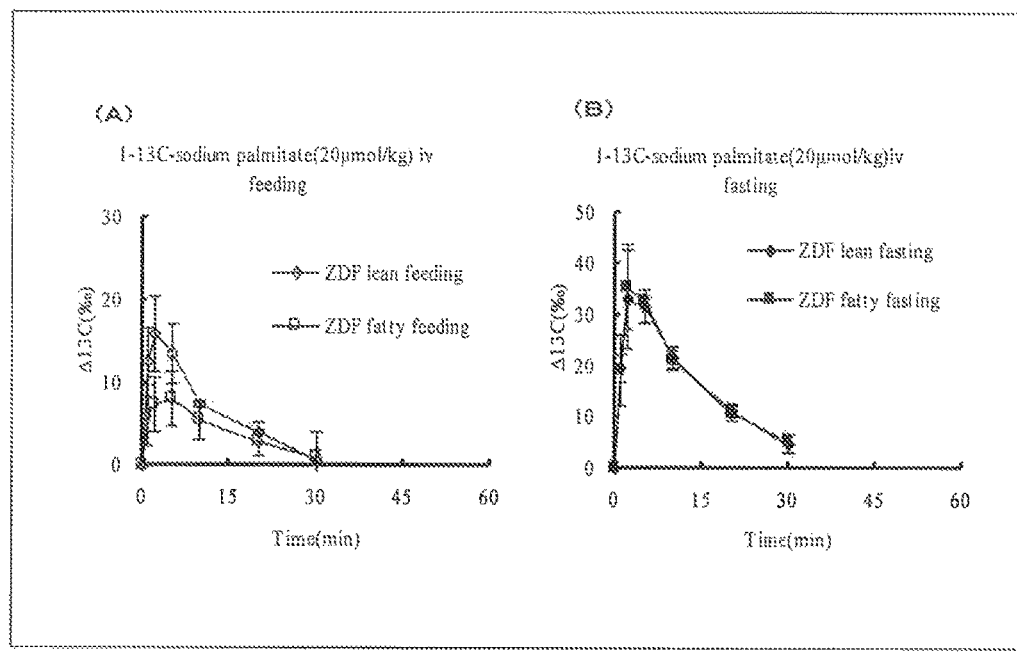
FIG. 11(A) shows transition of $\Delta^{13}C(‰)$ in the expired air measured after intravenous injection of a $1$-$^{13}C$-sodium palmitate solution to ZDF rats in a feeding state (Lean: -◇-, Fatty: -□-).
FIG. 11(B) shows transition of $\Delta^{13}C(‰)$ in the expired air measured after intravenous injection of a $1$-$^{13}C$-sodium palmitate solution to ZDF rats in a fasting state (Lean: -♦-, Fatty: -■-).

Further, as shown in Experimental Example 4 (FIGS. 10 and 11), the fatty acid metabolism ability is decreased in a test subject model having "insulin-nonresistant hyperinsulinemia" (FIG. 10: ZDF Fatty rat, FIG. 11: OLETF rat) in which sensitivity to insulin is not decreased despite the hyperinsulinemia, compared with a healthy subject (FIG. 10: ZDF Lean rat, FIG. 11: LETO rat). By administering labeled C-fatty acid to the "insulin-nonresistant hyperinsulinemia" test subject preferably in a feeding state, and performing step (b), as shown in FIGS. 10(A) and 11(A) (FIG. 10: graph of ZDF Fatty rat, FIG. 11: graph of OLETF rat), "the ratio of labeled $CO_2$ amount to unlabeled $CO_2$ amount contained in the expired air or the ratio of labeled $CO_2$ amount to total $CO_2$ amount contained in the expired air" ($\Delta\%$ $^{13}C$(atom %) or $\Delta^{13}C$ value(‰))(test subject value) obtained in step (b) Is lower (decreased) than "the ratio of labeled $CO_2$ amount to unlabeled $CO_2$ amount contained in the expired air or the ratio of labeled $CO_2$ amount to total $CO_2$ amount contained in the expired air" ($\Delta\%$ $^{13}C$(atom %) or $\Delta^{13}C$ value(‰)) obtained from a healthy subject (control value) (FIG. 10: ZDF Lean rat, FIG. 11: LETO rat) (Experimental Example 4). This reveals that the fatty acid metabolism in a test subject having hyperinsulinemia without insulin resistance (insulin-nonresistant hyperinsulinemia) is lower than that of a healthy subject. More specifically, the method of the present invention makes it possible to indirectly measure the presence or absence of insulin resistance in a hyperinsulinemia test subject from the fatty acid metabolism ability of the test subject, thereby discriminating between "insulin-nonresistant hyperinsulinemia" and "insulin resistant hyperinsulinemia." This method is also characterized in the highly accurate results that can be obtained shortly after the expired air collection (within 1 to 30 minutes, preferably within 1 to 15 minutes), as evident in FIGS. 10 and 11 showing the results of Experimental Example 4, in particular, FIGS. 10(A) and 11(A) showing the results in a feeding state.

Measurement of glucose metabolism ability known or conventional in this field (such as measurement of blood glucose level, insulin resistance test, and measurement of HbA1c) may be performed in parallel with the method of the present invention, which uses a breath test. By also performing measurement of glucose metabolism ability, it is possible to further judge and determine whether the test subject, who has been determined to be insulin-resistant by the method of the present invention, has borderline diabetes or diabetes (type II diabetes, gestational diabetes) accompanied by insulin resistance. Further, measurement of liver disease/liver function known or conventional in this field may be performed in parallel with the method of the present invention, which uses a breath test. By also using the measurement results regarding liver disease and/or liver function, the method of the present invention also makes it possible to judge and determine whether a test subject, who has been determined to be insulin-resistant by the method of the present invention, has liver disease (liver cirrhosis, NASH, NAFLD) accompanied by insulin resistance.

In this case, examples of test subject of the method of the present invention include humans or mammals other than humans who have the above diseases (borderline diabetes, diabetes, liver disease, liver dysfunction, etc., accompanied by insulin resistance), or may have these diseases. Further, the method of the present invention may be widely applied to humans or mammals other than humans for the purpose of detecting the presence or absence of insulin resistance, or for the purpose of detecting acquirement of those diseases together with the presence or absence of insulin resistance. With its high accuracy, the method of the present invention can be effectively used to judge and determine whether a test subject, who is not regarded as normal but does not have diabetes or borderline diabetes, has a state of low insulin sensitivity; and whether a test subject, who is not regarded as normal but does not have low insulin sensitivity, has hyperinsulinemia.

Based on a measurement value of a different index (blood glucose level), the test subject is diagnosed as "borderline diabetes" either when the fasting blood glucose level is 100 mg/dl to less than 126 mg/dl, preferably 110 mg/dl to less than 126 mg/dl, or when the 2-hour value of the oral glucose tolerance test (75 g OGTT) is 140 mg/dl to 199 mg/dl. Further, the test subject is diagnosed as "diabetic" either when (1) the fasting blood glucose level is 126 mg/dl or more, when (2) the 2-hour value of the oral glucose tolerance test (75 g OGTT) is 200 mg/dl or more, when (3) the random blood glucose level is 200 mg/dl or more, or when (4) hemoglobin A1c is 6.5% or more.

(IV) Method for Measuring Sugar/Fatty Acid Combustion Ratio

The sugar/lipid metabolism combustion ratio in the body may be evaluated from respiratory quotient that is generally calculated from the oxygen amount and the carbon dioxide amount excreted in expired air according to the formula below.

Respiratory Quotient (RQ)=carbon dioxide excretion amount per unit time/oxygen intake amount per unit time More specifically, the respiratory quotient upon intake of saccharide is RQ=1.0, and the respiratory quotient upon intake of lipid is RQ=0.7. Using these values of respiratory quotient, it is possible to determine which of sugar and lipid is used in the body in what proportion (combustion ratio).

The method for measuring sugar/fatty acid combustion ratio of the present invention (sugar/fatty acid combustion ratio measurement method) is a method for measuring a combustion ratio between sugar and fatty acid (sugar/fatty acid combustion ratio) in the body. This method of the present invention is useful since the method is capable of determining a desired sugar/fatty acid combustion ratio of a test subject in place of the hitherto-known respiratory quotient, and with higher accuracy than that of the known respiratory quotient.

The method for measuring sugar/fatty acid combustion ratio of the present invention can be roughly classified into the following three methods. (1) A method of determining a ratio $AUC_t$[labeled C-glucose]/$AUC_t$[labeled C-fatty acid], which is a ratio of $AUC(t)$ of $\Delta$-labeled C(‰) in a test subject obtained in a breath test after labeled C-glucose administration to $AUC(t)$ of $\Delta$-labeled C(‰) of the test subject obtained in a breath test after labeled C-fatty acid administration (t represents an expired air collection time, i.e., a time from the administration of labeled C-fatty acid to the collection of expired air; the same hereinafter).

(2) A method of determining a ratio [1/blood glucose level]/$AUC_t$[labeled C-fatty acid], which is a ratio of the reciprocal of blood glucose level (1/blood glucose level) of a test subject to $AUC(t)$ of $\Delta$-labeled C(‰) of the test subject obtained in a breath test after labeled C-fatty acid administration.

(3) A method of determining a ratio [1/blood glucose level]/$C_{max}$[labeled C-fatty acid], which is a ratio of the reciprocal of blood glucose level (1/blood glucose level) of a test subject to the maximum value $(Ct)(t=1$ to 30 min) of $\Delta$-labeled C(‰) of the test subject obtained in a breath test after labeled C-fatty acid administration.

These three methods are described below.
(1) Method for Determining "$AUC_t$[labeled C-Glucose]/$AUC_t$[Labeled C-Fatty Acid]"
(1-1) Method for Determining $AUC_t$[Labeled C-Fatty Acid]

In this method, $AUC_t$[labeled C-fatty acid] means [an area under the A-labeled C(‰)-expired air collection time t curve]($AUC_t$) obtained in the aforementioned breath test with labeled C-fatty acid administration of the present invention.

The "area under the $\Delta$-labeled C(‰)-expired air collection time t curve" ($AUC_t$) may be obtained from a graph showing changes over time of $\Delta$-labeled C(‰) obtained by the breath test with labeled C-fatty acid administration of the present invention. More specifically, the "area under the $\Delta$-labeled C(‰)-expired air collection time t curve" ($AUC_t$) may be obtained by calculating the area under the curve ($AUC_t$) of a graph in which the $\Delta^{13}$C(‰) obtained by the breath test with labeled C-fatty acid administration of the present invention is plotted on the ordinate axis, and the lapse of time after labeled C-fatty acid administration (expired air collection time: t) (min) is plotted on the abscissa axis.

The labeled C-fatty acid, dosage forms and administration methods of labeled C-fatty acid, and the calculation method of Δ-labeled C(‰) are as explained above in (III); the above descriptions can also be applied herein.

The expired air collection time (t) is an arbitrary time point within 1 to 60 minutes after labeled C-fatty acid administration, and any time point may be selected within this range. The expired air collection time (t) is preferably within 1 to 30 minutes, more preferably within 1 to 15 minutes, after labeled C-fatty acid administration.

(1-2) Method for Determining $AUC_t$[Labeled C-Glucose]

Further, in this method, $AUC_t$[labeled C-glucose] means [an area under the Δ-labeled C(‰)-expired air collection time t curve]($AUC_t$) that is obtained by a breath test with labeled C-glucose administration. The "area under the Δ-labeled C(‰)-expired air collection time t curve" ($AUC_t$) may be obtained from a graph showing changes over time of Δ-labeled C(‰) obtained by administering labeled C-glucose instead of labeled C-fatty acid in the aforementioned breath test of the present invention. More specifically, the "area under the Δ-labeled C(‰)-expired air collection time t curve" ($AUC_t$) may be obtained by calculating the area under the curve of a graph in which the $\Delta^{13}C(‰)$ obtained by the breath test with labeled C-glucose administration is plotted on the ordinate axis, and the lapse of time after labeled C-glucose administration (expired air collection time: t) (min) is plotted on the abscissa axis.

The expired air collection time (t) is an arbitrary time point within 1 to 120 minutes after labeled C-glucose administration, and any time point may be selected within this range. The expired air collection time (t) is preferably within 1 to 60 minutes, more preferably within 1 to 30 minutes, after labeled C-glucose administration. However, to determine "$AUC_t$ [labeled C-glucose]/$AUC_t$[labeled C-fatty acid]," the same expired air collection time (t) as that used in the calculation of $AUC_t$ [labeled C-fatty acid] is used.

The labeled C-glucose may be any glucose labeled with at least one isotope of C, wherein the glucose is converted in the body into labeled $CO_2$ gas that is excreted in expired air. The labeled C-glucose has a feature such that, after being administered to a test subject, the labeled C-glucose is metabolized according to glucose metabolism ability in the body and excreted in expired air in the form of carbon dioxide containing labeled C, which reflects the degree of glucose metabolism ability of the test subject. There is no particular limitation on isotopes used in labeling carbon atoms of glucose, and specific examples include $^{13}C$ and $^{14}C$. Such isotopes may be radioactive or non-radioactive; however, from the standpoint of safety, non-radioactive isotopes are preferable. For example, $^{13}C$ is desirable for use as such an isotope.

The isotope-labeled glucose is labeled in such a manner that at least a portion of the $CO_2$ formed through the glucose metabolic pathway is isotope-labeled. Examples of such glucose include compounds in which the carbon atom at at least one of the 1-position or the 6-position, the 2-position or the 5-position, and the 3-position or the 4-position of glucose is labeled with an isotope. Specific examples include 1-$^{13}C$-labeled glucose, 2-$^{13}C$-labeled glucose, and 3-$^{13}C$-labeled glucose. Glucose in which all of the carbon atoms at the 1-, 2-, 3-, 4-, 5-, and 6-positions are isotope-labeled may be used. Glucose in which the carbon atom at the 3-position or the 4-position is isotope-labeled (e.g., 3-$^{13}C$-labeled glucose and 4-$^{13}C$-labeled glucose) and glucose in which all of the carbon atoms at the 1-, 2-, 3-, 4-, 5-, and 6-positions are isotope-labeled are preferable.

There is no particular limitation on the method for labeling compounds such as glucose with isotopes such as $^{13}C$ or $^{14}C$, and a wide variety of commonly used methods may be employed. Such isotope-labeled compounds, particularly $^{13}C$-labeled glucose described in the Example 2, are commercially available as conveniently usable commercial products.

In the breath test, a composition containing labeled C-glucose may be administered as a test sample to a test subject. There is no particular limitation on the composition of the present invention in terms of its form, components other than the labeled C-glucose, proportion of each component, preparation method of the composition, etc., as long as the labeled C-glucose is absorbed in the body after administration, and excreted in expired air in the form of labeled carbon dioxide after metabolism. For example, the form of the composition may be an oral dosage form or an intravenous dosage form. Examples of oral dosage forms include any oral dosage forms, such as solutions (including syrup), suspensions, emulsions and like liquids; tablets (with and without coating), chewable tablets, capsules, pills, pulvis (powders), fine particles, granules, and like solids. Examples of intravenous dosage forms include any intravenous dosage forms, such as injections and drops (in liquid, suspension, or emulsion form). Oral dosage forms are preferable because they are non-invasive measurement methods; however, from the standpoint of obtaining high measurement accuracy, intravenous dosage forms are preferable. In this case, when the composition of the present invention is prepared in liquid, suspension, or emulsion form, for example, drops or injections, various carriers and/or additives suitable to such forms may be used in addition to purified water or water for injection. Examples of additives include additives commonly used, such as tonicity-adjusting agents (e.g., sodium chloride etc.), pH adjusters (e.g., hydrochloric acid, sodium hydroxide, etc.), buffers (e.g., boric acid, sodium monohydrogen phosphate, sodium dihydrogen phosphate, etc.), preservatives (e.g., benzalkonium chloride etc.), and thickeners (e.g., carboxyvinyl polymers etc.).

The form of the composition is not limited to a pharmaceutical preparation, as long as the composition contains the labeled C-glucose and does not adversely affect the effects of the present invention. The labeled C-glucose may be combined with any foodstuff and formed into solid food, fluid food, or liquid food. The composition of the present invention may substantially consist only of the labeled C-glucose, which is an active ingredient; however, as long as the effects of the present invention are not adversely affected, any pharmaceutically acceptable carriers and/or additives that are generally used in this field may be added as other components according to a pharmaceutical form (dosage form). In this case, there is no particular limitation on the amount of the labeled C-glucose contained as an active ingredient. For example, the amount of the labeled C-glucose is in the range of 1 to 95 wt % based on the total weight (100 wt %) of the composition, and is suitably controlled within this range.

The dose of the labeled C-glucose may be suitably adjusted for each case; for example, the amount of the labeled C-glucose per dose is, for example, in the range of 5 mg/body to 50 g/body, and preferably 10 mg/body to 25 g/body.

(1-3) "$AUC_t$[Labeled C-Glucose]/$AUC_t$[Labeled C-Fatty Acid]"

A sugar/fatty acid combustion ratio of a test subject may be measured from the ratio of $AUC_t$[labeled C-glucose] to AUC$_t$[labeled C-fatty acid](AUC$_t$[labeled C-glucose]/AUC$_t$[labeled C-fatty acid]) obtained above.

For example, in comparison of "AUC$_t$[labeled C-glucose]/AUC$_t$[labeled C-fatty acid]" of a test subject with "AUC$_t$[labeled C-glucose]/AUC$_t$[labeled C-fatty acid]" of a healthy subject having normal glucose metabolism ability and normal lipid metabolism ability (fatty acid metabolism ability), if "AUC$_t$[labeled C-glucose]/AUC$_t$[labeled C-fatty acid]" of the test subject is lower, it may be determined that the glucose metabolism ability of the test subject is decreased, or that the lipid metabolism ability (fatty acid metabolism ability) of the test subject is increased.

Figure 13:
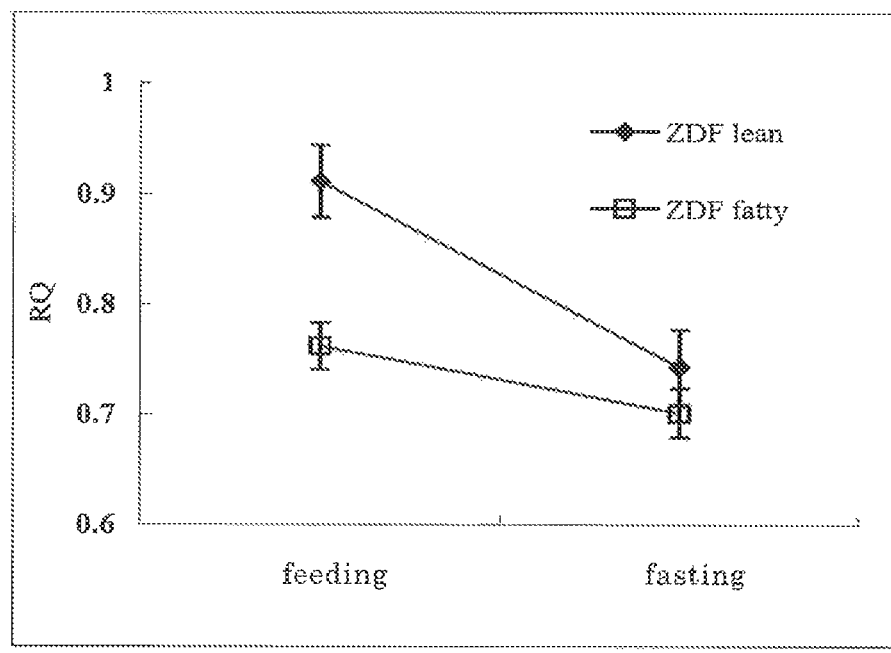
FIG. 13 shows measured average value±SD of respiratory quotient (RQ) of ZDF rats in fasting and feeding states (Lean: -◆-, Fatty: -□-) (Experimental Example 5).

The measurement is more specifically described below based on FIG. 13 showing the results of Experimental Example 5 described later.

FIG. 13 of Experimental Example 5 shows the results of comparison between a ratio of AUC$_t$[labeled C-glucose] to AUC$_t$[labeled C-fatty acid](AUC$_t$[labeled C-glucose]/AUC$_t$[labeled C-fatty acid]) of a diabetes test subject animal (ZDF Fatty rat) having glucose metabolic disorder (insulin resistance) obtained by the above method and a ratio (AUC$_t$[labeled C-glucose]/AUC$_t$[labeled C-fatty acid]) of a healthy subject animal (ZDF Lean rat) having normal glucose metabolism ability (sensitivity to insulin) obtained by the above method; the comparison was performed in a fasting state and a feeding state.

As shown in FIG. 13, the ratio "AUC$_t$[labeled C-glucose]/AUC$_t$[labeled C-fatty acid]" obtained from the diabetes test subject (ZDF Fatty rat) was significantly lower than that of the healthy subject (ZDF Lean rat) both in the fasting state and the feeding state; the difference between them is very clear. This revealed that the glucose metabolism ability (sensitivity to insulin) of the diabetes test subject is lower than the healthy subject, or that the lipid metabolism ability (fatty acid metabolism ability) of the diabetes test subject is increased so as to compensate the decrease.

(2) Method for Determining "[1/Blood Glucose Level]/AUC$_t$[Labeled C-Fatty Acid]"

(2-1) Method for Determining AUC$_t$[Labeled C-Fatty Acid]

The method for determining AUC$_t$[labeled C-fatty acid] is as described above; the above descriptions of the method can also be applied herein.

(2-2) Method for Determining [1/Blood Glucose Level]

The blood glucose level of a test subject may be determined according to the standard method. More specifically, blood glucose level of a test subject may be measured by an enzyme electrode method device (Life Check Sensor: Gunze Limited) using glucose dehydrogenase (GDH).

[1/blood glucose level] can be obtained from the reciprocal of the blood glucose level thus obtained above.

(2-3) "[1/Blood Glucose Level]/AUC$_t$[Labeled C-Fatty Acid]"

A sugar/fatty acid combustion ratio of a test subject may be measured from the ratio of [1/blood glucose level] to AUC$_t$[labeled C-fatty acid]([1/blood glucose level]/AUC$_t$[labeled C-fatty acid]) obtained above.

For example, in comparison of "[1/blood glucose level]/AUC$_t$[labeled C-fatty acid]" of a test subject with "[1/blood glucose level]/AUC$_t$[labeled C-fatty acid]" of a healthy subject having normal glucose metabolism ability (sensitivity to insulin) and normal lipid metabolism ability (fatty acid metabolism ability), if "[1/blood glucose level]/AUC$_t$[labeled C-fatty acid]" of the test subject is lower, it may be determined that the glucose metabolism ability (sensitivity to insulin) of the test subject is decreased, or that the lipid metabolism ability (fatty acid metabolism ability) of the test subject is increased.

Figure 15:
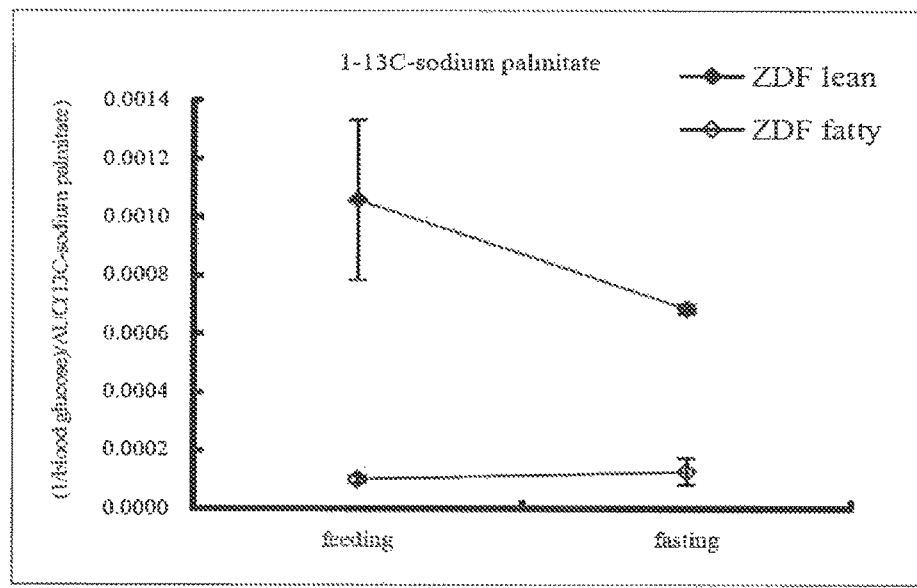
FIG. 15 shows a comparison between a fasting state and a feeding state with regard to a ratio ([1/blood glucose level]/AUC[1-$^{13}$C-sodium palmitate]) of reciprocal of blood glucose level (fasting state, feeding state) to $\Delta^{13}C(‰)$AUC (60 minutes) obtained by (f) 1-$^{13}$C-sodium palmitate solution administration (fasting state, feeding state) In Experimental Example 6 using ZDF rats (Lean and Fatty).

The measurement is more specifically described below based on FIG. 15 showing the results of Experimental Example 6 described later.

FIG. 15 of Experimental Example 6 shows the results of comparison between a ratio of [1/blood glucose level] to AUC$_t$[labeled C-fatty acid]([1/blood glucose level]/AUC$_t$[labeled C-fatty acid]) of a diabetes test subject animal (ZDF Fatty rat) having glucose metabolic disorder (insulin resistance) obtained by the above method and a ratio ([1/blood glucose level]/AUC$_t$[labeled C-fatty acid]) of a healthy subject animal (ZDF Lean rat) having normal glucose metabolism ability (sensitivity to insulin) obtained by the above method; the comparison was performed in a fasting state and a feeding state.

As shown in FIG. 15, the ratio "[1/blood glucose level]/AUC$_t$[labeled C-fatty acid]" obtained from the diabetes test subject (ZDF Fatty rat) was significantly lower than that of the healthy subject (ZDF Lean rat) both in the fasting state and the feeding state; the difference between them is very clear. This revealed that the glucose metabolism ability (sensitivity to insulin) of the diabetes test subject is lower than that of the healthy subject, or that the lipid metabolism ability (fatty acid metabolism ability) of the diabetes test subject is increased so as to compensate for the decrease.

(3) Method for Determining "[1/Blood Glucose Level]/Ct[Labeled C-Fatty Acid](t=1-30 Min)"

(3-1) Method for Determining [1/Blood Glucose Level]

The method for determining [1/blood glucose level] is as described above; the above descriptions of the method can also be applied herein.

(3-2) Method for Determining Ct[Labeled C-Fatty Acid] (t=1-30 Min)

In this method, Ct[labeled C-fatty acid] (t=1-30 min) means the value (Ct) of Δ-labeled C(‰) at an arbitrary expired air collection time (t), which is within 1 to 30 minutes from the labeled C-fatty acid administration and is obtained by the aforementioned breath test with labeled C-fatty acid administration of the present invention. The expired air collection time (t) is not limited, and may be any time point insofar as it is at least one time point between 1 to 30 minutes after the labeled C-fatty acid administration. The expired air collection time (t) is preferably at least one time point within 1 to 15 minutes, more preferably within 1 to 10 minutes after labeled C-glucose administration. The Ct[labeled C-fatty acid] (t=1-30 min) includes the maximum value ($C_{max}$) of Δ-labeled C(‰).

The Ct[labeled C-fatty acid] (t=1-30 min) may be determined by calculating Δ-labeled C(‰) using expired air obtained within 1 to 30 minutes, preferably 1 to 15 minutes, more preferably 1 to 10 minutes from the labeled C-fatty acid administration in the breath test with labeled C-fatty acid administration of the present invention.

Further, to determine the maximum value ($C_{max}$) of Δ-labeled C(‰) as one embodiment of Ct[labeled C-fatty acid] (t=1-30 min), a graph showing changes over time of Δ-labeled C(‰) obtained in the breath test with labeled C-fatty acid administration of the present invention can be used. More specifically, based on a graph in which the Δ$^{13}$C(‰) obtained by the breath test with labeled C-fatty acid administration of the present invention is plotted on the ordinate axis, and the lapse of time after labeled C-fatty acid administration (expired air collection time: t, wherein t=1-30 (min)) is plotted on the abscissa axis, the maximum value of Δ$^{13}$C(‰) peak is determined as $C_{max}$[labeled C-fatty acid].

The labeled C-fatty acid, dosage forms and administration methods of labeled C-fatty acid, and the calculation method of Δ-labeled C(‰) are as explained above in (III); the above descriptions can also be applied herein.

(3-3) "[1/Blood Glucose Level]/Ct[Labeled C-Fatty Acid] (t=1-30 Min)"

A sugar/fatty acid combustion ratio of a test subject can be determined from the ratio of [1/blood glucose level] to Ct[labeled C-fatty acid] (t=1-30 min) ([1/blood glucose level]/Ct[labeled C-fatty acid] (t=1-30 min)) obtained above.

For example, in comparison of "[1/blood glucose level]/Ct[labeled C-fatty acid] (t=1-30 min)" of a test subject with "[1/blood glucose level]/Ct[labeled C-fatty acid] (t=1-30 min)" of a healthy subject having normal glucose metabolism ability (sensitivity to insulin) and normal lipid metabolism ability (fatty acid metabolism ability), if "[1/blood glucose level]/Ct[labeled C-fatty acid] (t=1-30 min)" of the test subject is lower, it may be determined that the glucose metabolism ability (sensitivity to insulin) of the test subject is decreased, or that the lipid metabolism ability (fatty acid metabolism ability) of the test subject is increased.

EXAMPLES

Examples and Experimental Examples are described below to further clarify the present invention. However, the present invention is not limited to these Examples etc.

Experimental Example 1

(1) Preparation of 1-$^{13}$C-Sodium Palmitate Solution

1-$^{13}$C-sodium palmitate was dissolved in hydrous ethanol at about 80° C. at a concentration of 500 μmol/mL. The resulting solution was added to 20% BSA that had been heated to 37° C. and stirred and dissolved so that the 1-$^{13}$C-sodium palmitate concentration was 20 μmol/2 ml, thereby preparing a 1-$^{13}$C-sodium palmitate solution (the same procedure is used in the Experimental Examples below).

(2) Experiment Method

Rats (male, Zucker rat) were used as experimental animals. The rats that were fasted from the previous day of the test were divided into two groups: oral administration group and intravenous administration group (each group, n=3), and the 1-$^{13}$C-sodium palmitate solution (20 μmol/2 mL) prepared in (1) was orally and intravenously administered at a dosage of 2 mL/kg. Expired air was collected at each time point (t minutes) from a time point before administration (0 minutes) to a time point 180 minutes after the administration, and Δ$^{13}$C(‰) was determined from the concentration of $^{13}$CO$_2$ in the expired air using an expired air analysis mass spectrometer (ABCA: product of SerCon).

The value of Δ$^{13}$C(‰) was determined by measuring a concentration ratio $^{13}$CO$_2$/$^{12}$CO$_2$ in the expired air (δ$^{13}$C value) at each time point (t minutes) from a time point before the 1-$^{13}$C-sodium palmitate administration (0 minutes) to a time point after the administration, and calculating the Δ$^{13}$C(‰) value from the difference between the δ$^{13}$C value (δ$^{13}$Ct) at each point (t) and the δ$^{13}$C value before the administration (δ$^{13}$Co) (δ$^{13}$Ct-δ$^{13}$Co) (the same calculation is used in the Experimental Examples below).

(3) Experiment Results

FIG. 1 shows transition of Δ$^{13}$C(‰) in the expired air measured after oral administration (po) or intravenous administration (iv) of 1-$^{13}$C-sodium palmitate solution. In the figure, the ordinate axis denotes Δ$^{3}$C(‰) in the expired air, and the abscissa axis denotes expired air collection time (t minutes) after 1-$^{13}$C-sodium palmitate administration.

As shown in FIG. 1, in the oral administration group (-◇-), the measurement value of Δ$^{13}$C(‰) had little variation among respective measurement times; however, in the intravenous administration group (—■—), Δ$^{13}$C(‰) peak was observed in a relatively early time point (within 10 minutes after the administration).

The results revealed that 1-$^{13}$C-sodium palmitate is excreted in expired air as $^{13}$CO$_2$. The results also revealed that the fat combustion under fasting conditions can be determined by intravenously administering 1-$^{13}$C-sodium palmitate solution, i.e., not by orally administering 1-$^{13}$C-sodium palmitate solution.

Experimental Example 2: Evaluation of Insulin Resistance Using Various $^{13}$C-Labeled Compounds (1) Preparation of Various $^{13}$C-Labeled Compound-Containing Solutions (a) U-$^{13}$C-Glucose Solution U-$^{13}$C-glucose was dissolved in physiological saline at a concentration of 50 μmol/mL, thereby preparing a U-$^{13}$C-glucose solution.

(b) 1-$^{13}$C-Sodium Acetate Solution

1-$^{13}$C-sodium acetate was dissolved in physiological saline at a concentration of 50 μmol/mL, thereby preparing a 1-$^{13}$C-sodium acetate solution.

(c) 1-$^{13}$C-Sodium Octanoate Solution

1-$^{13}$C-sodium octanoate was dissolved in physiological saline at a concentration of 50 μmol/mL, thereby preparing a 1-$^{13}$C-sodium octanoate solution.

(d) 1-$^{13}$C-Lauric Acid Solution

1-$^{13}$C-lauric acid was dissolved in hydrous ethanol at about 80° C. at a concentration of 500 μmol/mL. The resulting solution was added to 20% BSA that had been heated to 37° C., and stirred and dissolved so that the 1-$^{13}$C-lauric acid concentration was 20 μmol/2 ml, thereby preparing a 1-$^{13}$C-lauric acid solution. (e) 1-$^{13}$C-sodium palmitate solution Using the same method as in Experimental Example 1, 1-$^{13}$C-sodium palmitate was dissolved in hydrous ethanol at a concentration of 20 μmol/2 ml, thereby preparing a 1-$^{13}$C-sodium palmitate solution.

(f) 1-$^{113}$C-oleic acid solution 0.5 g of oleic acid, 0.5 g of soybean oil, and 0.12 g of purified egg-yolk lecithin were placed in a plastic tube. After dissolution, a glycerin solution (24.7 mg/mL) was added in an amount of 0.5 mL at a time until the mixture was emulsified. After obtaining an emulsion of about 9 mL, the emulsion was filtrated with a 1.2 μm filter, and diluted with water in a measuring cylinder to 10 mL total.

The oleic acid content of the liquid was measured, and diluted with a glycerin solution (22 mg/mL), thereby obtaining a 5.65 mg/mL (20 μmol/mL) solution.

(2) Evaluation of Insulin Resistance

(2.1) Experiment Method

The animals (A) and (B) below were used as experimental animals.

(A) ZDF rat (male, Lean (18 weeks, blood glucose level and insulin value under a fasting condition were 73 mg/dL and 1.0 ng/mL, respectively, blood glucose level and insulin value under a feeding condition were 98 mg/dL and 3.9 ng/mL, respectively), and Fatty (18 weeks, blood glucose level and insulin value under a fasting condition were 369 mg/dL and 1.7 ng/mL, respectively, and blood glucose level and insulin value under a feeding condition were 474 mg/dL and 13.6 ng/mL, respectively)).

(B) ZDF rat (male, Lean (13 weeks, blood glucose level and insulin value under a fasting condition were 63.8 mg/dL and 0.21 ng/mL, respectively, and blood glucose level and insulin value under a feeding condition were 111.5 mg/dL and 2.26 ng/mL, respectively), and Fatty (13 weeks, blood glucose level and insulin value under a fasting condition were 240.3 mg/dL and 1.97 ng/mL, respectively, and blood glucose level and insulin value under a feeding condition were 595.8 mg/dL and 2.77 ng/mL, respectively)).

ZDF Fatty rat is an insulin-resistant test subject animal that has a low sensitivity to insulin, and develops a pathological condition similar to human adult type II diabetes and diabetes complication. In contrast, ZDF Lean rat is a healthy subject animal having normal blood glucose level and normal sensitivity to insulin. Lean and Fatty rats (A) were divided into a fasting group in which the rats were fasted from the previous day, and a feeding group. Each group was further divided into 5 groups, and (a) U-$^{13}$C-glucose solution, (b) 1-$^{13}$C-sodium acetate solution, (c) 1-$^{13}$C-sodium octanoate solution, (f) 1-$^{13}$C-oleic acid solution (all 1 ml/kg each), (d) 1-$^{13}$C-lauric acid solution, or (e) 1-$^{13}$C-sodium palmitate solution (2 ml/kg each) prepared above was intravenously administered. For (a) to (e), expired air was collected from rats (A), and for (f), expired air was collected and rats (B) (each group, n=3).

Expired air was obtained at time points (t minutes) from a time point before the administration of solutions (a) to (f) (0 minutes) to a time point 60 minutes after the administration, and $\Delta^{13}C(‰)$ was determined from $^{13}CO_2$ concentration in the expired air using an expired air analysis mass spectrometer (ABCA: product of SerCon).

(2-2) Experiment Results

(2-2-1) Administration of U-$^{13}$C-Glucose Solution

FIG. 2 shows transition of $\Delta^{13}C(‰)$ in the expired air measured after intravenous administration of U-$^{13}$C-glucose solution to ZDF rats (Lean and Fatty). FIG. 2(A) shows the results of Lean rats, and FIG. 2(B) shows the results of Fatty rats. In the figure, the ordinate axis denotes $\Delta^{13}C(‰)$ in the expired air, and the abscissa axis denotes expired air collection time (t minutes) after U-$^{13}$C-glucose solution administration.

As shown in the results of FIG. 2, since Lean rats are healthy subjects, they use saccharide in the feed as an energy source under feeding conditions. Therefore, the value of $\Delta^{3}C(‰)$ is higher than that under fasting conditions. In contrast, since Fatty rats are insulin-resistant test subjects and cannot use saccharide for genetic reasons, there was little difference in the transition of $\Delta^{13}C(‰)$ between the fasting state and the feeding state, i.e., the transition was almost the same.

(2-2-2) Administration of 1-$^{13}$C-Sodium Acetate Solution

Figure 3:
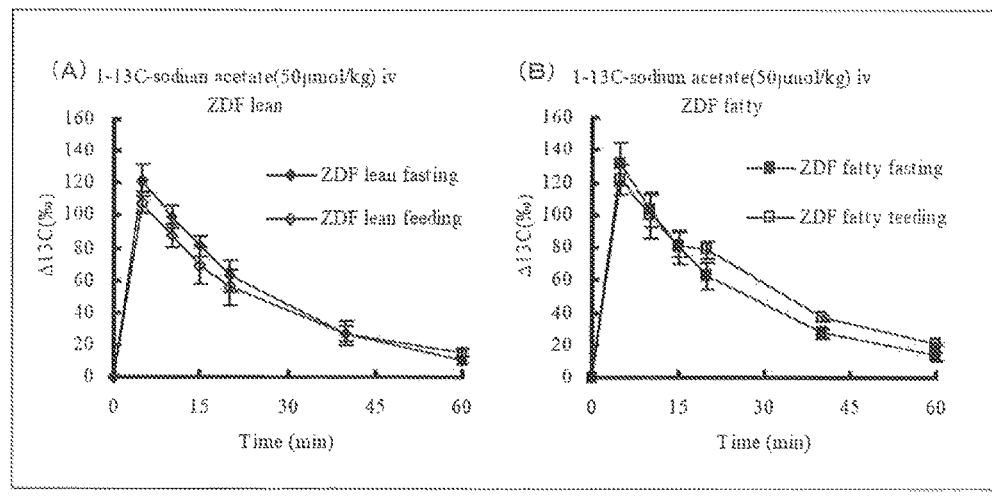
FIG. 3 shows transition of $\Delta^{13}C(‰)$ in the expired air measured after intravenous injection of a $1$-$^{13}C$-sodium acetate solution to ZDF rats in a fasting or feeding state (Lean and Fatty).

FIG. 3 shows transition of $\Delta^{13}C(‰)$ in the expired air measured after intravenous administration of 1-$^{13}$C-sodium acetate solution to ZDF rats (Lean and Fatty). FIG. 3(A) shows the results of Lean rats and FIG. 3(B) shows the results of Fatty rats. In the figure, the ordinate axis denotes $\Delta^{13}C(‰)$ in the expired air, and the abscissa axis denotes expired air collection time (t minutes) after U-$^{13}$C-sodium acetate solution administration. As shown in the results of FIG. 3, there was little difference between the results of Lean rats and the results of Fatty rats, i.e., the transition of $\Delta^{13}C(‰)$ was almost the same in each group.

(2-2-3) Administration of 1-$^{13}$C-Sodium Octanoate Solution

Figure 4:
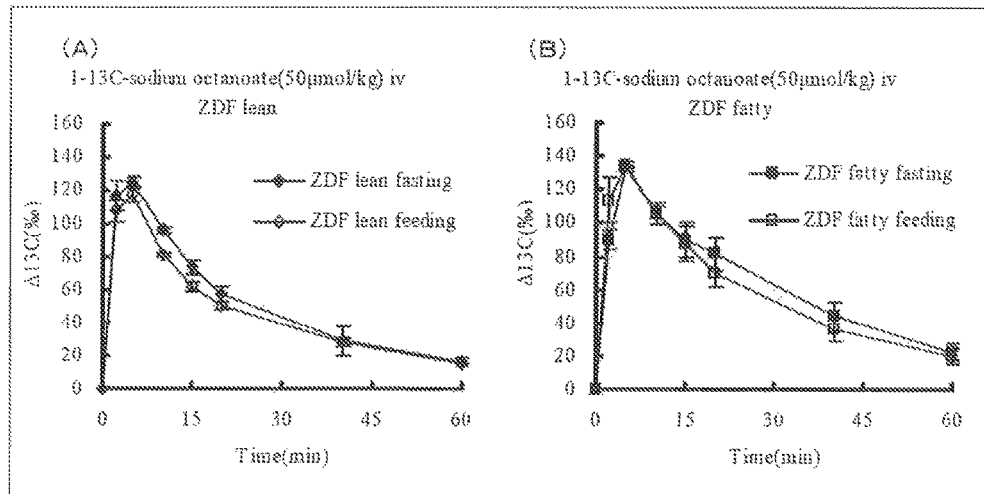
FIG. 4 shows transition of $\Delta^{13}C(‰)$ in the expired air measured after intravenous injection of a $1$-$^{13}C$-sodium octanoate solution to ZDF rats in a fasting or feeding state (Lean and Fatty).

FIG. 4 shows transition of $\Delta^{13}C(‰)$ in the expired air measured after intravenous administration of 1-$^{13}$C-sodium octanoate solution to ZDF rats (Lean and Fatty). FIG. 4(A) shows the results of Lean rats, and FIG. 4(B) shows the results of Fatty rats. In the figure, the ordinate axis denotes $\Delta^{13}C(‰)$ in the expired air, and the abscissa axis denotes expired air collection time (t minutes) after U-$^{13}$C-sodium octanoate solution administration. As shown in the results of FIG. 4, there was little difference between the results of Lean rats and the results of Fatty rats, i.e., the transition of $\Delta^{13}C(‰)$ was almost the same in each group.

(2-2-4) Administration of 1-$^{13}$C-Lauric Acid Solution

Figure 5:
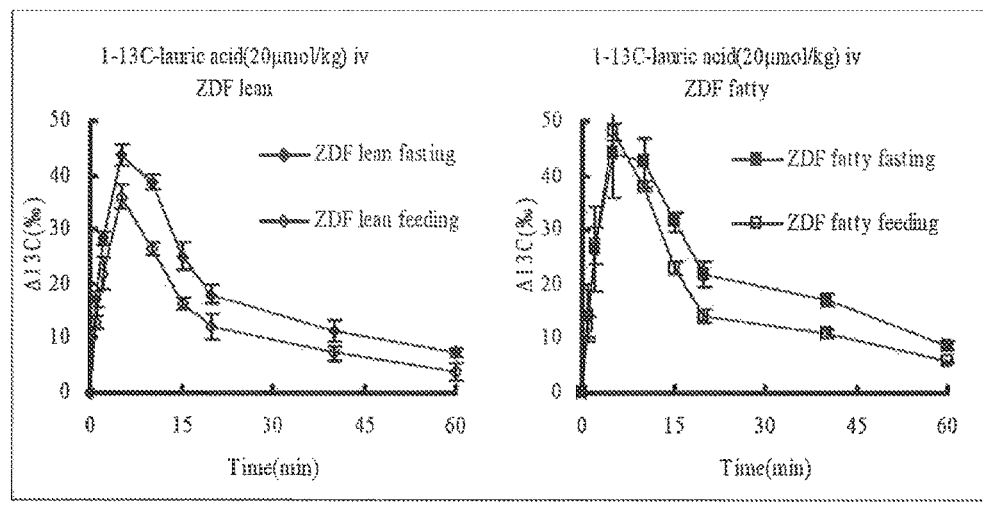
FIG. 5 shows transition of $\Delta^{13}C(‰)$ in the expired air measured after intravenous injection of a $1$-$^{13}C$-lauric acid solution to ZDF rats in a fasting or feeding state (Lean and Fatty).

FIG. 5 shows transition of $\Delta^{13}C(‰)$ in the expired air measured after intravenous administration of 1-$^{13}$C-lauric acid solution to ZDF rats (Lean and Fatty). In the figure, the ordinate axis denotes $\Delta^{13}C(‰)$ in the expired air, and the abscissa axis denotes expired air collection time (t minutes) after 1-$^{13}$C-lauric acid solution administration. FIG. 5(A) shows the results of Lean rats, and FIG. 5(B) shows the results of Fatty rats. As shown in FIG. 5, although transition of $\Delta^{13}C(‰)$ was different between the fasting group and the feeding group of the healthy subjects (Lean) after Intravenous administration of 1-$^{13}$C-lauric acid, in particular, during a period until 10 minutes after the intravenous administration, there was no difference between the fasting group and the feeding group of insulin-resistant test subjects (Fatty). In comparison between healthy subjects (Lean) and insulin-resistant test subjects (Fatty), their difference was particularly significant in the transition of $\Delta^{13}C(‰)$ in the feeding group, in particular, during a period until 15 minutes after the intravenous administration, showing a tendency that $\Delta^{13}C(‰)$ of the insulin-resistant test subjects (Fatty) was higher than that of the healthy subjects (Lean).

(2-2-5) 1-$^{13}$C-Sodium Palmitate Solution

Figure 6:
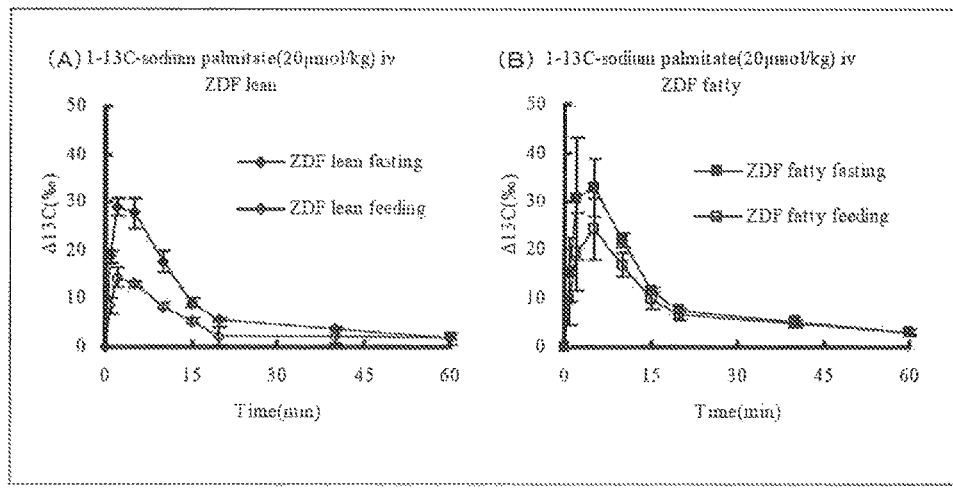
FIG. 6 shows transition of $\Delta^{13}C(‰)$ in the expired air measured after intravenous injection of a $1$-$^{13}C$-sodium palmitate solution to ZDF rats in a fasting or feeding state (Lean and Fatty).

FIG. 6 shows transition of $\Delta^{13}C(‰)$ in the expired air measured after intravenous administration of a 1-$^{13}$C-sodium palmitate solution to ZDF rats (Lean and Fatty). FIG. 6(A) shows the results of Lean rats, and FIG. 6(B) shows the results of Fatty rats. In the figure, the ordinate axis denotes $\Delta^{13}C(‰)$ in the expired air, and the abscissa axis denotes expired air collection time (t minutes) after 1-$^{13}$C-sodium palmitate solution administration:

(2-2-6) Administration of 1-$^{13}$C-Oleic Acid Solution

Figure 7:
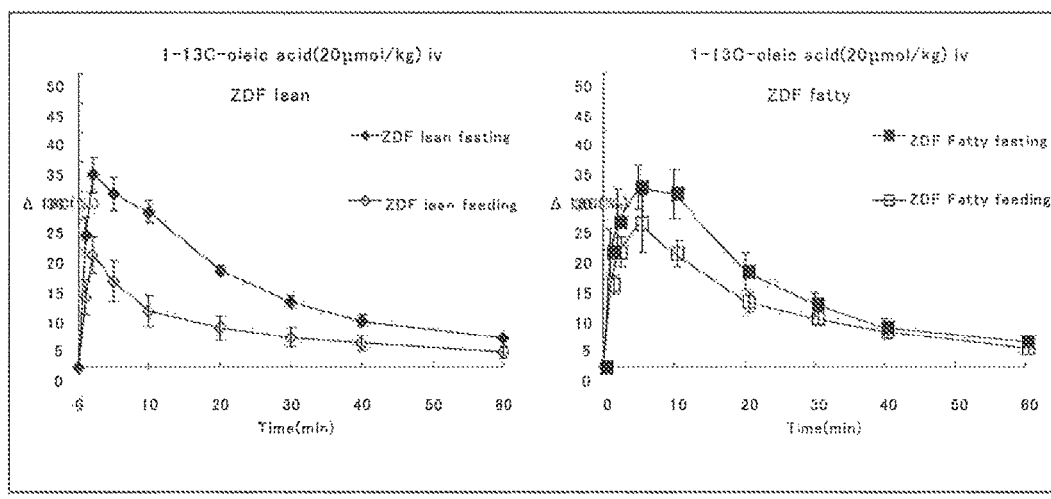
FIG. 7 shows transition of $\Delta^{13}C(‰)$ in the expired air measured after intravenous injection of a $1$-$^{13}C$-oleic acid solution to ZDF rats in a fasting or feeding state (Lean and Fatty).

FIG. 7 shows transition of $\Delta^{13}C(‰)$ in the expired air measured after intravenous administration of a 1-$^{13}$C-oleic apid solution to ZDF rats (Lean and Fatty). FIG. 7(A) shows the results of Lean rats, and FIG. 7(B) shows the results of Fatty rats. In the figure, the ordinate axis denotes $\Delta^{13}C(‰)$ in the expired air, and the abscissa axis denotes expired air collection time (t minutes) after administration of 1-$^{13}$C-oleic acid solution.

As shown in FIG. 6, regarding the transition of $\Delta^{3}C(‰)$ after the intravenous administration of 1-$^{13}$C-sodium palmitate, the $\Delta^{13}C(‰)$ values of healthy subjects (Lean) and the insulin-resistant test subjects (Fatty) were both higher in the fasting (hunger) state than in the feeding state. It was thus revealed that there is a difference in energy use in the body between the feeding state and the fasting state. A comparison between healthy subjects (Lean) and insulin-resistant test subjects (Fatty) revealed that their difference was particularly significant in the transition of $\Delta^{13}C(‰)$ in the feeding group, in particular, during a period until 15 minutes after the intravenous administration, showing a tendency that $\Delta^{13}C(‰)$ of the insulin-resistant test subjects (Fatty) was higher than that of the healthy subjects (Lean).

As shown in FIG. 7, regarding the transition of $\Delta^{13}C(‰)$ after the intravenous administration of 1-$^{13}$C-oleic acid, the $\Delta^{13}C(‰)$ values of healthy subjects (Lean) and the insulin-resistant test subjects (Fatty) were both higher in the fasting (hunger) state than in the feeding state. It was thus revealed that there is a difference in energy use in the body between the feeding state and the fasting state. In comparison between healthy subjects (Lean) and insulin-resistant test subjects (Fatty), their difference was particularly significant in the transition of $\Delta^{13}C(‰)$ in the feeding group, in particular, during a period until 30 minutes after the intravenous administration, showing a tendency that $\Delta^{13}C(‰)$ of the insulin-resistant test subjects (Fatty) was higher than that of the healthy subjects (Lean).

Further, the difference in energy use in the body between the fasting state and the feeding state is clearer than the case of administering a U-$^{13}$C-glucose solution in (2-2-1). Thus, switching of energy source can be more precisely monitored. These results revealed that by intravenously administering 1-$^{13}$C-palmitic acid or a salt thereof, or 1-$^{13}$C-oleic acid or a salt thereof in a fasting state and a feeding state, preferably in a feeding state, and performing a breath test, it is possible to determine the presence or absence of insulin resistance.

Experimental Example 3: Evaluation of Insulin Resistance Using 1-$^{13}$C-Sodium Palmitate Solution

(1) Experiment Method

LETO rats (male) (25 weeks, blood glucose level and insulin value under a fasting condition: 80 mg/dL and 1.4 ng/mL; blood glucose level and insulin value under a feeding condition: 105 mg/dL and 3.2 ng/mL) and OLETF rats (male) (25 weeks, blood glucose level and insulin value under a fasting condition: 101 mg/dL and 1.1 ng/mL; blood glucose level and insulin value under a feeding condition: 198 mg/dL and 14.4 ng/mL) were used as experimental animals. OLETF rats are type II diabetes test subject animal with obesity or/and fatty liver, and LETO rats serve as a control thereof (healthy subjects). OLETF rats had normal blood glucose under fasting conditions; however, they had hyperinsulinemia and high blood glucose under feeding conditions. This shows that they are in a state of hidden diabetes. The results revealed that OLETF rats are hyperinsulinemia rats having low sensitivity to insulin, and that they are therefore regarded as insulin-resistant test subject animals.

These rats were divided into a fasting group in which the rats were fasted from the previous day, and a feeding group. 1-$^{13}$C-sodium palmitate solution prepared in Experimental Example 2 was intravenously administered (2 ml/kg) to each group (each group, n=3). Expired air was collected at time points (t minutes) from a time point before the 1-$^{13}$C-sodium palmitate solution administration (0 minutes) to a time point 60 minutes after the administration, and $\Delta^{13}C(‰)$ was determined from the $^{13}CO_2$ concentration in the expired air using an expired air analysis mass spectrometer (ABCA: product of SerCon).

(2) Experiment Results

Figure 8:
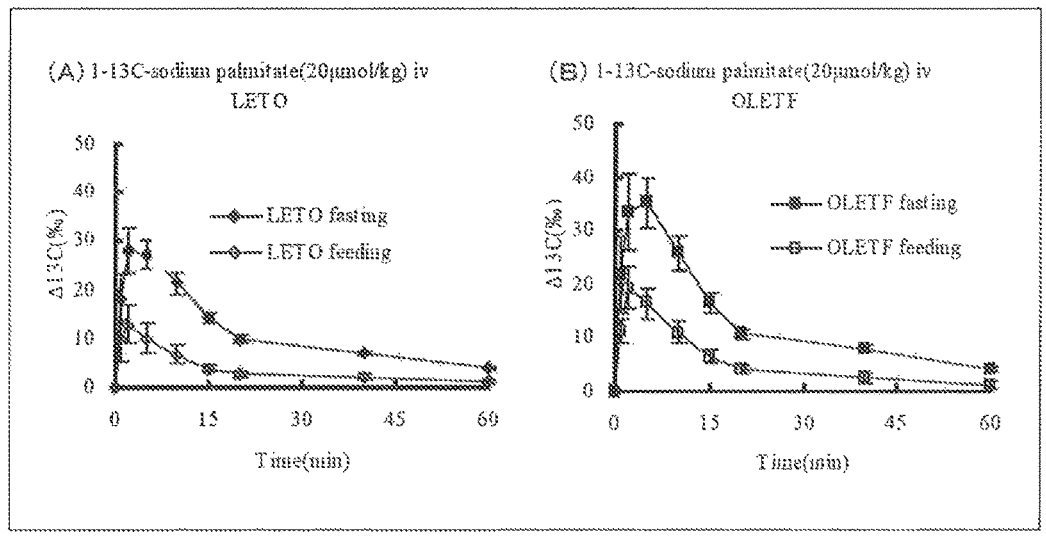
FIG. 8 shows transition of $\Delta^{13}C(‰)$ in the expired air measured after intravenous administration of a $1$-$^{13}C$-sodium palmitate solution to each group (fasting and feeding groups) of LETO and OLETF rats.
Figure 9:
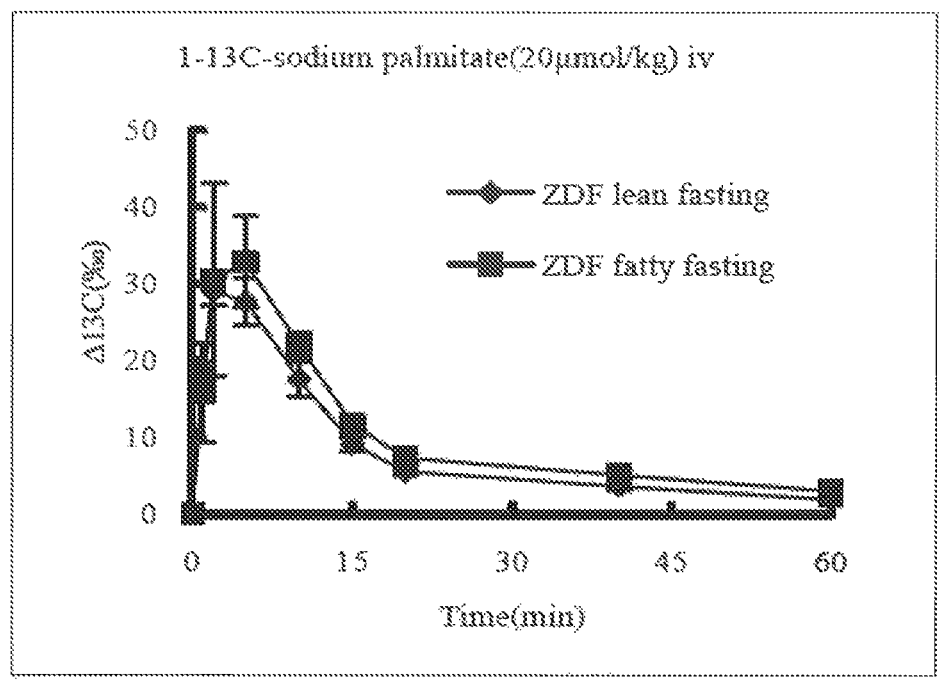
FIG. 9(A) shows transition of $\Delta^{3}C(‰)$ in the expired air measured after intravenous injection of a $1$-$^{13}C$-sodium palmitate solution to ZDF rats in a fasting state (Lean: -♦-, Fatty: -■-).
FIG. 9(B) shows transition of $\Delta^{13}C(‰)$ in the expired air measured after intravenous injection of a $1$-$^{13}C$-sodium palmitate solution to ZDF rats in a feeding state (Lean: -◇-, Fatty: -□-).
Figure 9:
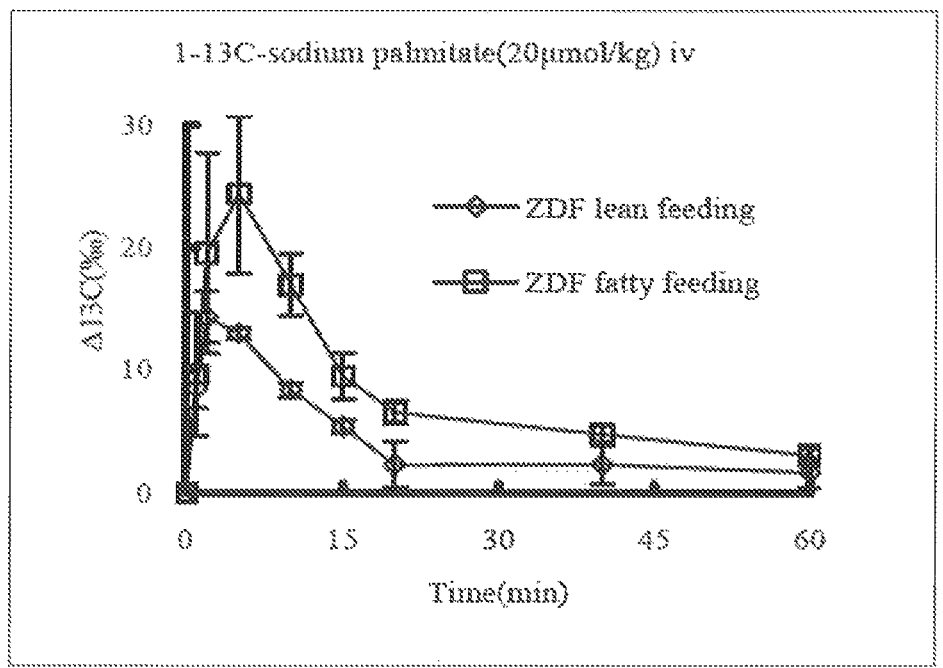

FIG. 8 shows the transition of $\Delta^{13}C(‰)$ in the expired air measured after intravenous administration of 1-$^{13}$C-sodium palmitate solution to each group (fasting group and feeding group) of LETO rats as healthy subjects and OLETF rats as insulin-resistant test subjects. (A) denotes the results of LETO rats, and (B) denotes the results of OLETF rats. In the figure, the ordinate axis denotes $\Delta^{13}C(‰)$ in the expired air, and the abscissa axis denotes expired air collection time (t minutes) after the 1-$^{13}$C-sodium palmitate solution administration.

As shown in FIG. 8, regarding the transition of $\Delta^{13}C(‰)$ after the intravenous administration of 1-$^{13}$C-sodium palmitate, the $\Delta^{13}C(‰)$ values of LETO rats and OLETF rats were both higher in the fasting (hunger) state than in the feeding state, as in the results of Experimental Example 2(2)(2-2-5). It was thus revealed that there is a difference in energy use in the body between the feeding state and the fasting state. A comparison between healthy subjects (LETO) and insulin-resistant test subjects (OLETF) having liver disease revealed that their difference was significant in the transition of $\Delta^{13}C(‰)$ both in the fasting group and the feeding group, in particular, during a period until 15 minutes after the intravenous administration, showing a tendency that $\Delta^{13}C(‰)$ of the insulin-resistant test subjects (OLETF) having liver disease was higher than that of the healthy subjects (LETO).

The results demonstrated that the breath test using 1-$^{13}$C-palmitic acid makes it possible to sensitively monitor insulin resistances of not only insulin-resistant test subjects who have developed diabetes, but also test subjects having hidden diabetes accompanied by liver disease.

FIGS. 9(A) and 9(B) respectively show the transitions of $\Delta^{13}C(‰)$ after intravenous administration of 1-$^{13}$C-sodium palmitate to ZDF rats (male, Lean and Fatty) in a fasting state and a feeding state. FIGS. 10(A) and 10(B) respectively show the transitions of $\Delta^{13}C(‰)$ after intravenous administration of 1-$^{13}$C-sodium palmitate to LETO rats as healthy subject and OLETF rats as insulin-resistant test subject having liver disease in a fasting state and a feeding state. As shown in FIGS. 9(A) and 10(A), although the difference in glucose metabolism ability (sensitivity to insulin) can be determined between the healthy subjects and insulin-resistant test subjects having liver disease also in the fasting state, their difference can be determined based on a further greater difference by performing the measurement in a feeding state, as shown in FIGS. 9(B) and 10(B).

Experimental Example 4: Evaluation of Hyperinsulinemia not Accompanied by Insulin Resistance (Insulin-Nonresistant-Hyperinsulinemia)–

(1) Experiment Method

As animals at a stage of pre-onset of insulin resistance (low sensitivity to insulin), OLETF rats (11 weeks, blood glucose level and insulin value under a fasting condition: 104 mg/dL and 0.6 ng/mL; blood glucose level and insulin value under a feeding condition: 124 mg/dL and 2.7 ng/mL), and ZDF Fatty rats (11 weeks, blood glucose level and insulin value under a fasting condition: 91 mg/dL and 3.4 ng/mL; blood glucose level and insulin value under a feeding condition: 116 mg/dL and 19.0 ng/mL) were used. Further, as the control (healthy subjects), LETO rats (11 weeks, blood glucose level and insulin value under a fasting condition: 57 mg/dL and 0.3 ng/mL; blood glucose level and insulin value under a feeding condition: 98 mg/dL and 1.4 ng/mL) and ZDF Lean rats (11 weeks, blood glucose level and insulin value under a fasting condition: 72 mg/dL and 0.3 ng/mL; blood glucose level and insulin value under a feeding condition: 113 mg/dL and 1.7 ng/mL) were used. The blood glucose levels of these animals at a stage of pre-onset of insulin resistance (OLETF rats and ZDF Fatty rats) were within a normal range; however, the animals had hyperinsulinemia. Therefore, these animals are referred to as test subjects having hyperinsulinemia not accompanied by insulin resistance, simply as "insulin-nonresistant hyperinsulinemia test subjects".

These rats were divided into a fasting group in which the rats were fasted from the previous day, and a feeding group. 1-$^{13}$C-sodium palmitate solution prepared in Experimental Example 2 was intravenously administered (2 ml/kg) to each group (each group, n=3). Expired air was collected at time points (t minutes) from a time point before the 1-$^{13}$C-sodium palmitate solution administration (0 minutes) to a time point 30 minutes after the administration, and $\Delta^{13}$C(‰) was determined from the $^{13}CO_2$ concentration in the expired air using an expired air analysis mass spectrometer (ABCA: product of SerCon).

(2) Experiment Results

FIG. 11 shows transition of $\Delta^{13}$C(‰) in the expired air measured after intravenous administration of a 1-$^{13}$C-sodium palmitate solution to each group of ZDF rats (male, Lean and Fatty) (feeding group, fasting group). FIG. 11 (A) shows the results of the feeding group and FIG. 11(B) shows the results of the fasting group. In the figure, the ordinate axis denotes $\Delta^{13}$C(‰) in the expired air, and the abscissa axis denotes expired air collection time (t minutes) after the 1-$^{13}$C-sodium palmitate solution administration.

Figure 12:
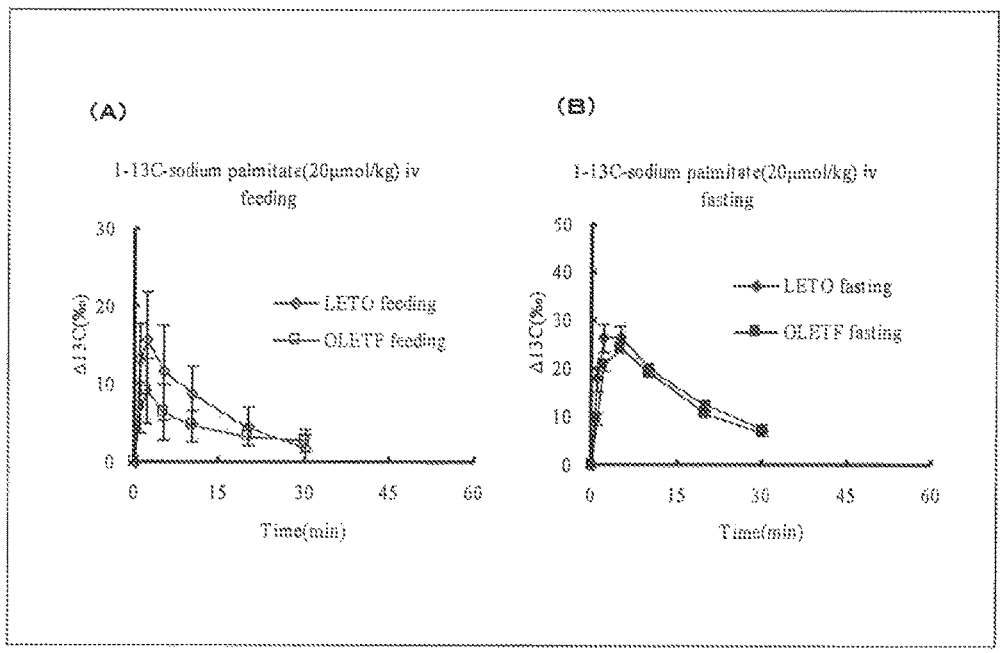
FIG. 12(A) shows transition of $\Delta^{13}C(‰)$ in the expired air measured after intravenous injection of a 1-$^{13}$C-sodium palmitate solution to LETO rats (-◇-) and OLETF rats (-□-) in a feeding state.
FIG. 12(B) shows transition of $\Delta^{13}C(‰)$ in the expired air measured after intravenous injection of a 1-$^{13}$C-sodium palmitate solution to LETO rats (-◆-) and OLETF rats (-■-) in a fasting state.

FIG. 12 shows respective transitions of $\Delta^{13}$C(‰) of LETO rats and OLETF rats after intravenous administration of 1-$^{13}$C-sodium palmitate solution in a feeding state and a fasting state. FIG. 12(A) shows the results of the feeding group and FIG. 12(B) shows the results of the fasting group.

As shown in FIGS. 11(B) and 12(B), at the stage of pre-onset of insulin resistance, little difference in transition of $\Delta^3$C(‰) was observed between the healthy subject and the insulin-nonresistant hyperinsulinemia test subject in the fasting state. However, as shown in FIGS. 11(A) and 12(A), it was confirmed that the $\Delta^{13}$C(a) value of the insulin-nonresistant hyperinsulinemia test subject is significantly lower than that of the healthy subject in the feeding state. This pattern is opposite the patter shown in Experimental Example 2 with regard to the insulin-resistant test subject who has developed diabetes, and the pattern shown in Experimental Example 3 with regard to the insulin-resistant test subject with hidden diabetes accompanied by liver disease (the pattern in which the transition of $\Delta^3$C(‰) after 1-$^{13}$C-sodium palmitate solution administration is significantly higher in the insulin-resistant test subject than in a healthy subject) (FIGS. 7 to 10). This revealed that the fatty acid metabolism of the insulin-nonresistant hyperinsulinemia patients is decreased, in contrast to the insulin-resistant patients. This revealed that the presence or absence of insulin resistance in hyperinsulinemia patients can be determined by using, as an index, the presence or the absence of increase and decrease in fatty acid metabolism. More specifically, when the fatty acid metabolism in a hyperinsulinemia patient is determined to be higher than that of a healthy subject in a breath test using a labeled C-fatty acid, the hyperinsulinemia patient is determined to have low sensitivity to insulin (insulin resistance is present, insulin resistant hyperinsulinemia); in contrast, when the fatty acid metabolism in a hyperinsulinemia patient is lower than that of a healthy subject in the same breath test, it is determined that the sensitivity to insulin of the hyperinsulinemia patient is not decreased (no insulin resistance, insulin-nonresistant hyperinsulinemia).

Experimental Example 5: Evaluation of Respiratory Quotient

As experimental animals, rats (male, ZDF rats, Lean and Fatty) were divided into two groups (fasting group and oral administration group). The fasting group was fasted from the previous day of the experiment. The oral administration group was placed in an expired air analysis chamber; than, after 40 minutes, they received glucose dissolved in water (2 g/4 mL) by oral administration at a dose of 4 mL/kg (n=1).

The respiratory quotient was calculated from the oxygen amount and the carbon dioxide amount excreted in expired air in each group according to the formula below using a biogas analysis mass spectrometer (ARCO-2000: Arco System Inc.).

Respiratory Quotient (RQ)=carbon dioxide excretion amount per unit time/oxygen intake amount per unit time The respiratory quotient of saccharide is RQ=1.0, and the respiratory quotient of lipid is RQ=0.7. Therefore, based on the respiratory quotient obtained by the above formula, it is possible to measure which of sugar and lipid is used in the body in what proportion.

FIG. 13 shows the respiratory quotient average value±SD measured for ZDF rats (Lean and Fatty).

The results revealed that the healthy subjects (Lean) use saccharide as an energy source in the feeding state, whereas the insulin-resistant test subjects (Fatty) who have developed diabetes do not use saccharide. The results also showed that there is little difference between these two groups in the fasting state.

Experimental Example 6: Sugar/Fatty Acid Combustion Ratio

The sugar/fatty acid combustion ratio was calculated using the results of (a) U-$^{13}$C-glucose solution administration and the results of (e)1-$^{13}$C-sodium palmitate solution administration obtained in Experimental Example 2.

(1) Saccharide/Fatty Acid Combustion Ratio (A)

Figure 14:
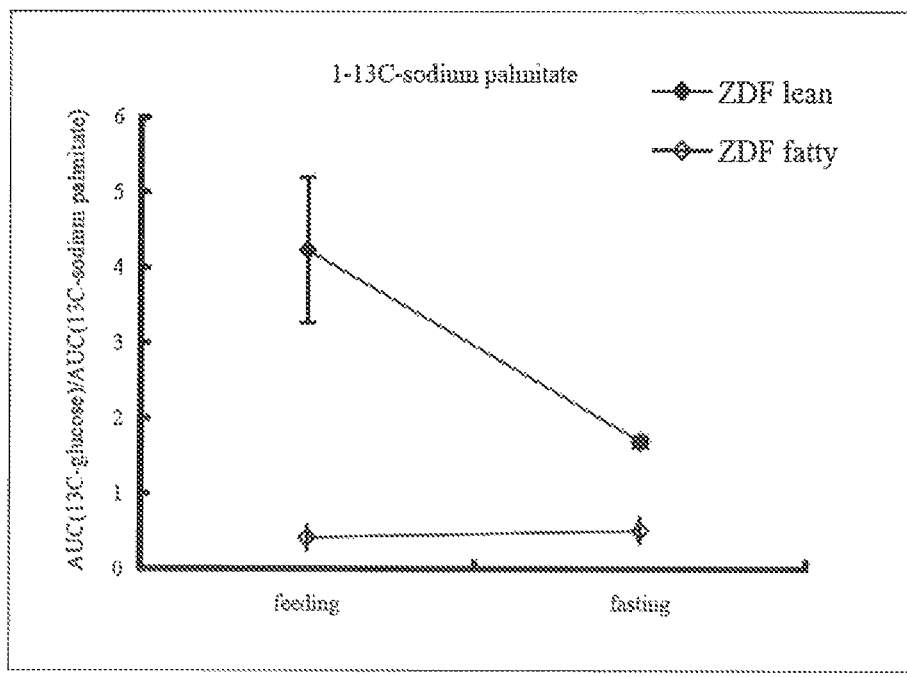
FIG. 14 shows a comparison between a fasting state and a feeding state with regard to a ratio (AUC[U-$^{13}$C-glucose]/AUC[1-$^{13}$C-sodium palmitate]) of $\Delta^{13}C(‰)$AUC (120 minutes) obtained by (a) U-$^{13}$C-glucose solution administration (fasting state, feeding state) to $\Delta^{13}C(‰)$AUC (60 minutes) obtained by (f) 1-$^{13}$C-sodium palmitate solution administration (fasting state, feeding state) obtained in Experimental Example 6 using ZDF rats (Lean and Fatty).

FIG. 14 shows a comparison between a fasting state and a feeding state with regard to a ratio (AUC[$^{13}$-C-glucose]/AUC[1-$^{13}$C-sodium palmitate]) of AUC (120 minutes) of $\Delta^{13}$C(‰) obtained by (a) U-$^{13}$C-glucose solution administration (fasting state, feeding state) to AUC (60 minutes) of $\Delta^{13}$C(‰) obtained by (e)1-$^{13}$C-sodium palmitate solution administration (fasting state, feeding state) obtained in Experimental Example 2 using ZDF rats (Lean and Fatty). This ratio (AUC[$^{13}$C-glucose]/AUC[1-$^{13}$C-sodium palmitate]) represents a sugar/fatty acid combustion ratio.

Since U-$^{13}$C-glucose has 6 carbons, ⅙ AUC120 minutes value was used. Since the administration amount of 1-$^{13}$C-sodium palmitate was 20 μmol/kg, AUC60 minutes value was multiplied by 2.5 to be consistent with the administration amount 50 μmol/kg of U-$^{13}$C-glucose.

As shown in FIG. 14, for the respiratory quotient (RQ), the difference between healthy subjects (Lean) and the insulin-resistant test subjects (Fatty) who have developed diabetes was not clear in the fasting state. This reveals that the respiratory quotient (RQ) is incapable of accurately determine which of saccharide and fatty acid is used in the test subject as the energy source in the fasting state. In contrast, according to the "AUC[U-$^{13}$C-glucose]/AUC[1-$^{13}$C-fatty acid]" calculated from the results of the breath test using labeled C-glucose and the breath test using labeled C-fatty acid, as shown in FIG. 14, the difference between the healthy subjects (Lean) and the insulin-resistant test subjects (Fatty) who have developed diabetes is clear both in the fasting state and the feeding state. This reveals that it is possible, both in the fasting state and the feeding state, to accurately measure which of saccharide and fatty acid is used as the energy source in the test subject. More specifically, the above method makes it possible to measure which of saccharide and fatty acid is used as the energy source, in place of and more sensitively than respiratory quotient.

Further, as shown in FIG. 14, the difference in "AUC[U-$^{13}$C-glucose]/AUC[1-$^{13}$C-fatty acid]" of the insulin-resistant test subjects (Fatty) who have developed diabetes between the fasting state and the feeding state is significantly smaller than that of the healthy subjects (Lean). Therefore, by measuring the difference in "AUC[U-$^{13}$C-glucose]/AUC[1-$^{13}$C-fatty acid]" of a test subject between the fasting state and the feeding state, it is possible to measure decrease in insulin sensitivity (insulin resistance) of the test subject with higher accuracy.

(2) Saccharide/Fatty Acid Combustion Ratio (B)

FIG. 15 shows a comparison between a fasting state and a feeding state with regard to a ratio ([1/blood glucose level]/AUC[1-$^{13}$C-sodium palmitate]) of reciprocal of blood glucose level (fasting state, feeding state) to AUC (60 minutes) of $\Delta^{13}$C(‰) obtained by (e) 1-$^{13}$C-sodium palmitate solution administration (fasting state, feeding state) in Experimental Example 2 using ZDF rats (Lean and Fatty). The ratio ([1/blood glucose level]/AUC[1-$^{13}$C-sodium palmitate]) represents a sugar/fatty acid combustion ratio.

As in FIG. 14, it is possible to determine which of saccharide and fatty acid is used as the energy source in the healthy subjects (Lean) and in the insulin-resistant test subjects (Fatty) who have developed diabetes both in the fasting state and the feeding state. This reveals that simply performing measurement using 1-$^{13}$C-sodium palmitate serves as a substitute for respiratory quotient, and that, further, the measurement is more sensitive than respiratory quotient.

Further, as shown in FIG. 15, the difference in "[1/blood glucose level]/AUC[1-$^{13}$C-fatty acid]" of the insulin-resistant test subjects (Fatty) who have developed diabetes between the fasting state and the feeding state is significantly smaller than that of the healthy subjects (Lean). Therefore, by measuring the difference in "[1/blood glucose level]/AUC[1-$^{13}$C-fatty acid]" of a test subject between the fasting state and the feeding state, it is possible to measure insulin-resistant glucose tolerance of the test subject with higher accuracy.

(3) Saccharide/Fatty Acid Combustion Ratio(C)

FIG. 15 shows a comparison between a fasting state and a feeding state with regard to a ratio ([1/blood glucose level]/Ct [1-$^{13}$C-sodium palmitate]) of reciprocal of blood glucose level (fasting state, feeding state) to Ct of $\Delta^{13}$C(‰) obtained by (e)1-$^{13}$C-sodium palmitate solution administration (fasting state, feeding state) obtained in Experimental Example 2 using ZDF rats (Lean and Fatty). Herein, the time point where the $\Delta^{13}$C(‰) value is maximum was used as expired air collection time (t). More specifically, the conditions t=2 minutes and t=5 minutes were respectively used for the healthy subjects (Lean) in a fasting state and a feeding state, and the conditions t=2 minutes and t=5 minutes were respectively used for the diabetes test subjects (Fatty) in a fasting state and a feeding state.

This ratio ([1/blood glucose level]/Ct) represents a sugar/fatty acid combustion ratio.

Figure 16:
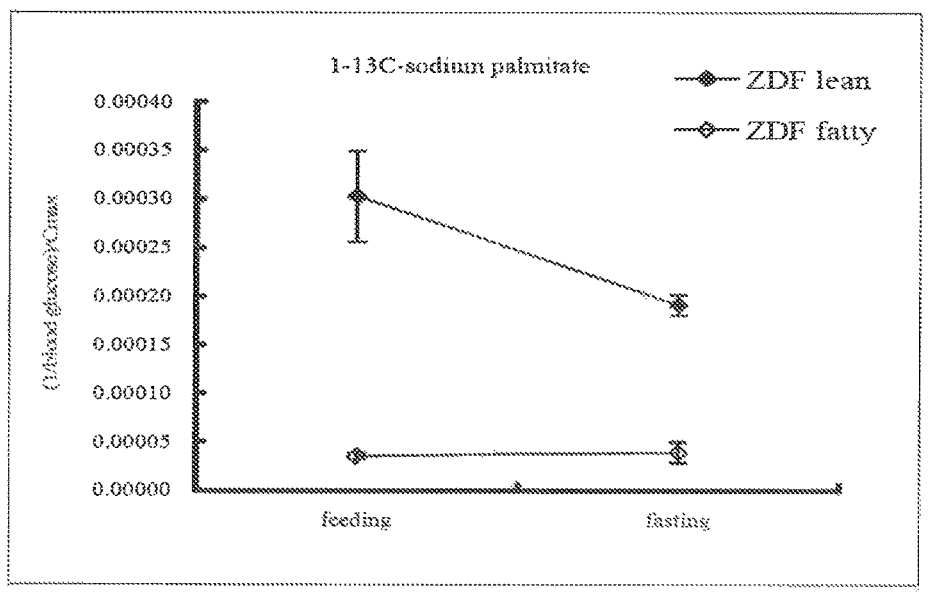
FIG. 16 shows a comparison between a fasting state and a feeding state with regard to a ratio ([1/blood glucose level]/$C_{max}$[1-$^{13}$C-sodium palmitate]) of reciprocal of blood glucose level (fasting state, feeding state) to $\Delta^{13}C(‰)C_{max}$ obtained by (f) 1-$^{13}$C-sodium palmitate solution administration (fasting state, feeding state) in Experimental Example 6 using ZDF rats (Lean and Fatty).

As shown in FIG. 16, it is possible to determine which of saccharide and fatty acid is used as the energy source in the healthy subjects (Lean) and in the diabetes test subject (Fatty) both in a fasting state and a feeding state, as in FIGS. 14 and 15. This reveals that simply performing measurement using 1-$^{13}$C-sodium palmitate at only one time point between 1 minute to 30 minutes after the 1-$^{13}$C-sodium palmitate administration serves as a substitute for respiratory quotient, and that the measurement is more sensitive than respiratory quotient.

Further, as shown in FIG. 16, the difference in "[1/blood glucose level]/Ct [1-$^{13}$C-fatty acid] (t=1-30 min)" of the diabetes test subjects (Fatty) between the fasting state and the feeding state is significantly smaller than that of the healthy subjects (Lean). Therefore, by measuring the difference in "[1/blood glucose level]/$C_{max}$ [1-$^{13}$C-fatty acid] (t=1-30 min)" of a test subject between the fasting state and the feeding state, it is possible to measure decrease in insulin sensitivity (insulin resistance) of the test subject with higher accuracy.

Experimental Example 7: (1) Preparation of 3-$^3$C-Glucose and 1-$^{13}$C-Sodium Palmitate Mixed Solution 1-$^{13}$C-sodium palmitate was dissolved in hydrous ethanol at about 80° C. at a concentration of 500 μmol/mL. The resulting solution was added to 20% BSA that had been heated to 37° C., and stirred. A 3-$^{13}$C-glucose solution was further added thereto, thereby preparing a mixed solution of 3-$^{13}$C-glucose (50 μmol/2 mL) and 1-$^{13}$C-sodium palmitate (20 μmol/2 mL) (hereinafter referred to as a "glucose/palmitic acid mixed solution").

(2) Experiment Method

Rats (male LETO and male OLETF) were used as experimental animals.

OLETF rats are diabetes test subjects with obesity and fatty liver, i.e., insulin-resistant test subjects, and LETO rats serve as a control (healthy subjects). The rats were divided into a control group (blood glucose level under feeding conditions: 108 mg/dL), a mild diabetes group (blood glucose level under feeding conditions: 166 mg/dL), and a severe diabetes group (blood glucose level under feeding conditions: 281 mg/dL), and the glucose/palmitic acid mixed solution prepared in (1) was intravenously administered to each group under feeding conditions at a dosage of 2 ml/kg (n=1).

Afterward, expired air was collected at a time point before the intravenous administration of glucose/palmitic acid mixed solution (0 minutes) and time points after the administration (t minutes), and $\Delta^{13}C(‰)$ was determined from the $^{13}CO_2$ concentration in the expired air using an expired air analysis mass spectrometer (ABCA: product of SerCon).

(3) Experiment Results

Figure 17:
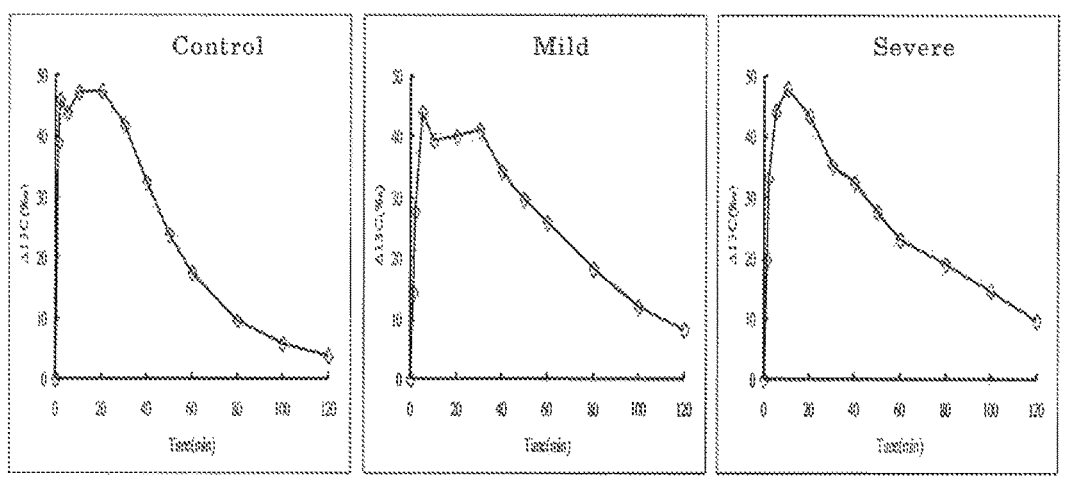
FIG. 17 shows the transitions of $\Delta^{13}C(‰)$ calculated from the $^{13}CO_2$ concentrations measured by the breath test after intravenously administering a mixed solution of 3-$^{13}$C glucose and 1-$^{13}$C-sodium palmitate to, from left to right, a control group (blood glucose level under feeding conditions: 108 mg/dL), a mild diabetes group (blood glucose level under feeding conditions: 166 mg/dL), and a severe diabetes group (blood glucose level under feeding conditions: 281 mg/dL).

FIG. 17 shows the results. FIG. 17 shows the transitions of $\Delta^{13}C(‰)$ calculated from the $^{13}CO_2$ concentrations measured by the breath test after intravenously administering the glucose/palmitic acid mixed solution to, from left to right, the control group (blood glucose level under feeding conditions: 108 mg/dL), the mild diabetes group (blood glucose level under feeding conditions: 166 mg/dL), and the severe diabetes group (blood glucose level under feeding conditions: 281 mg/dL). In the figure, the ordinate axis denotes $\Delta^{13}C(‰)$ in the expired air, and the abscissa axis denotes expired air collection time (t minutes) after the intravenous administration.

The measured values shown in FIG. 17 are well matched with the simulation results (not shown), thereby showing that the degree of progression of diabetes (control→mild diabetes→severe diabetes), i.e., the degree of progression of low sensitivity to insulin (increase in insulin resistance), can be monitored based on the transition of $\Delta^{13}C(‰)$ of the measured values. Further, by performing model analysis (pharmacokinetics), it is also possible to divide the measured values obtained from the administration of glucose/palmitic acid mixed solution into individual expired air reactions of glucose and palmitic acid.

The invention claimed is:

1. A method for measuring insulin resistance of a test subject, comprising
determining an area under a Δ-labeled C(‰)-expired air collection time t curve, based on a glucose metabolism ability measurement method having steps (i) and (ii) below (hereinafter referred to as "AUCt[labeled C-glucose]"),
determining an area under a Δ-labeled C(‰)-expired air collection time t curve, based on a method having steps (a) and (b) below (hereinafter referred to as "AUCt[labeled C-fatty acid]"),
using a value obtained by dividing the AUCt[labeled C-glucose] by the AUCt[labeled C-fatty acid] (AUCt[labeled C-glucose]/AUCt[labeled C-fatty acid]) as an index for the sugar/fatty acid combustion ratio,
determining a first index of the sugar/fatty acid combustion ratio under a fasting condition and a second index of the sugar/fatty acid combustion ratio under a feeding condition from the test subject, and
determining a difference between the first index and the second index, wherein the test subject's insulin resistance is measured,
wherein
the method in which AUCt[labeled C-glucose] is determined has the steps of:
(i) intravenously administering a composition to a test subject and collecting expired air, the composition comprising, as an active ingredient, glucose labeled with at least one isotope of carbon, so that the glucose is converted in the body into labeled carbon dioxide that is excreted in expired air; and
(ii) determining the ratio of labeled $CO_2$ amount to unlabeled $CO_2$ amount contained in expired air or the ratio of labeled $CO_2$ amount to total $CO_2$ amount contained in expired air, and
the method in which AUCt[labeled C-fatty acid] is determined has the steps of:
(a) intravenously administering a composition comprising a $C_{12-38}$ fatty acid or a salt thereof labeled with at least one isotope of carbon to a test subject and collecting expired air, so that the $C_{12-38}$ fatty acid or salt thereof is converted in the body into labeled carbon dioxide that is excreted in expired air; and
(b) determining the ratio of labeled $CO_2$ amount to unlabeled $CO_2$ amount contained in expired air or the ratio of labeled $CO_2$ amount to total $CO_2$ amount contained in expired air.

2. A method for measuring insulin resistance of a test subject, comprising
determining an area under a Δ-labeled C(‰)-expired air collection time t curve, based on a method having steps (a) and (b) below (herein referred to as "AUCt[labeled C-fatty acid]"),
determining a blood glucose level of the test subject,
using a value obtained by dividing the reciprocal of the blood glucose level (1/blood glucose level) of the test subject by the AUCt[labeled C-fatty acid] (1/blood glucose level/AUCt[labeled C-fatty acid]) as an index for the sugar/fatty acid combustion ratio,
determining a first index of the sugar/fatty acid combustion ratio under a fasting condition and a second index of the sugar/fatty acid combustion ratio under a feeding condition for the test subject, and
determining a difference between the first index and the second index, wherein the test subject's insulin resistance is measured,
wherein
the method in which AUCt[labeled C-fatty acid] is determined has the steps of:
(a) intravenously administering a composition comprising a $C_{12-38}$ fatty acid or a salt thereof labeled with at least one isotope of carbon to a test subject and collecting expired air, so that the $C_{12-38}$ fatty acid or a salt thereof is converted in the body into labeled carbon dioxide that is excreted in expired air; and
(b) determining the ratio of labeled $CO_2$ amount to unlabeled $CO_2$ amount contained in expired air or the ratio of labeled $CO_2$ amount to total $CO_2$ amount contained in expired air.

3. A method for measuring insulin resistance of a test subject, comprising
determining Ct[labeled C-fatty acid] (t=1-30 min) of Δ-labeled C(‰), based on a method having steps (a) and (b) below,
determining a blood glucose level of the test subject,
using a value obtained by dividing the reciprocal of the blood glucose level (1/blood glucose level) of the test subject by Ct[labeled C-fatty acid] (t=1-30 min) ([1/ blood glucose level]/Ct[labeled C-fatty acid] (t=1-30 min)), as an index for the sugar/fatty acid combustion ratio, determining a first index of the sugar/fatty acid combustion ratio under a fasting condition and a second index of the sugar/fatty acid combustion ratio under a feeding condition for the test subject, and determining a difference between the first index and the second index, wherein the test subject's insulin is measured, wherein the method in which Ct[labeled C-fatty acid] (t=1-30 min) is determined has the steps of:

(a) intravenously administering a composition comprising a $C_{12-38}$ fatty acid or a salt thereof labeled with at least one isotope of carbon to a test subject and collecting expired air at least one time point between 1 to 30 minutes after the composition administration, so that the $C_{12-38}$ fatty acid or a salt thereof is converted in the body into labeled carbon dioxide that is excreted in expired air; and (b) determining the ratio of labeled $CO_2$ amount to unlabeled $CO_2$ amount contained in expired air or the ratio of labeled $CO_2$ amount to total $CO_2$ amount contained in expired air.

4. The method according to any one of claims 1 to 3, wherein the isotope of $C_{12-38}$ fatty acid is $^{13}C$.

5. The method according to any one of claims 1 to 3, wherein the $C_{12-38}$ fatty acid is a $C_{12-18}$ saturated fatty acid or a $C_{18}$ unsaturated fatty acid.

6. The method according to any one of claims 1 to 3, wherein the $C_{12-38}$ fatty acid is at least one member selected from the group consisting of lauric acid, myristic acid, pentadecylic acid, stearic acid, oleic acid, and palmitic acid.

7. The method according to any one of claims 1 to 3, wherein the test subject has at least one condition selected from the group consisting of borderline diabetes, type II diabetes, liver cirrhosis, non-alcoholic steatohepatitis, and non-alcoholic fatty liver disease.

8. The method according to any one of claims 1 to 3, further comprising: comparing a difference between the first index and the second index obtained from the test subject (test subject value) to a difference between the first index and the second index obtained from a healthy subject having a normal insulin resistance (control value), wherein when the test subject value is smaller than the control value, the insulin sensitivity of the test subject is decreased (insulin resistance).

* * * * *